(12) United States Patent
Forman et al.

(10) Patent No.: US 6,906,057 B1
(45) Date of Patent: Jun. 14, 2005

(54) METHODS FOR MODULATING FXR RECEPTOR ACTIVITY

(75) Inventors: Barry M. Forman, Newport Beach, CA (US); Richard L. Beard, Newport Beach, CA (US); Roshantha A. Chandraratna, Laguna Hills, CA (US)

(73) Assignees: Allergan, Inc., Irvine, CA (US); City of Hope National Medical Center, Duarte, CA (US)

( * ) Notice: Subject to any disclaimer, the term of this patent is extended or adjusted under 35 U.S.C. 154(b) by 422 days.

(21) Appl. No.: 09/590,447

(22) Filed: Jun. 9, 2000

Related U.S. Application Data

(60) Provisional application No. 60/138,968, filed on Jun. 11, 1999.

(51) Int. Cl.$^7$ .................... A61K 31/551; A61K 31/553; A61K 31/554; A61K 31/55
(52) U.S. Cl. ............................. 514/211.08; 514/211.15; 514/217.05; 514/218
(58) Field of Search ....................... 514/211.08, 211.15, 514/217.05, 218

(56) References Cited

U.S. PATENT DOCUMENTS

| | | |
|---|---|---|
| 5,053,523 A | 10/1991 | Chandraratna |
| 5,278,318 A | 1/1994 | Chandraratna |
| 5,324,744 A | 6/1994 | Chandraratna |
| 5,346,895 A | 9/1994 | Chandraratna |
| 5,348,972 A | 9/1994 | Chandraratna |
| 5,348,975 A | 9/1994 | Chandraratna |
| 5,407,937 A | 4/1995 | Chandraratna |
| 5,663,347 A | 9/1997 | Chandraratna |
| 5,776,699 A | 7/1998 | Klein et al. |
| 5,808,083 A | 9/1998 | Johnson et al. |
| 5,877,207 A | 3/1999 | Klein et al. |

FOREIGN PATENT DOCUMENTS

| | | |
|---|---|---|
| WO | WO 00/40965 | 7/2000 |

OTHER PUBLICATIONS

Evans et al, "The Steroid and Thyroid Hormone Receptor Superfamily" Science vol. 240: 889–895 (May 1988).

Mangelsdorf et al, The Retinoid Receptors in The Retinoids: Biology, Chemistry, and Medicine Ch.8 (Sporn et al, eds. 2d ed, Raven Press Ltd. 1994).

Nagpal et al, "Retinoids as Anti–Cancer Agents", Current Pharm. Design 2:295–316 (1996).

Foreman et al, "Identification of a Nuclear Receptor That is Activated by Farnesol Metabolites", Cell vol. 81: 687–693 (1995).

Meigs et al, "Regulation of 3–Hydroxy–3–methylglutaryl–Coenzyme A Reductase Degradation by the Nonsterol Mevalonate Metabolite Farnesol in Vivo*", J. Biol. Chem. vol. 271: 7916–7922 (1996).

Chiang, "Regulation of Bile Acid Synthesis", Front. Biosci. 3: d176–193 (Feb. 1998).

Wang et al, "Endogenous Bile Acids Are Ligands for the Nuclear Receptor FXR/BAR", Molecular Cell vol. 3: 543–553 (May 1999).

Seed, "An LFA–3 cDNA encodes a phospholipid–linked membrane protein homologuous to its receptor CD2", Nature vol. 329: 840–842 (Oct. 1987).

(Continued)

Primary Examiner—San-ming Hui
(74) Attorney, Agent, or Firm—Hamilton, Brook, Smith & Reynolds, P.C.

(57) ABSTRACT

Methods for modulating the activity of the mammalian FXR receptor. The methods include methods of treating a hyper- or hypocholesterolemic mammal comprising contacting the mammal with synthetic compounds having FXR receptor activity.

30 Claims, 9 Drawing Sheets

OTHER PUBLICATIONS

Umesono et al, "Direct Repeats as Selective Response Elements for the Thyroid Hormone, Retinoic Acid, and Vitamin $D_3$ Receptors", vol. Cell 65: 1255–1266 (1991).

Sadowski et al, "A vector for expressin GAL4(1—1470 fusions in mammalian cells", Nucleic Acids Research, vol. 17, No. 18: 7539 (1989).

Forman et al, "15–Deoxy–$^{12,\ 14}$–Prostoglandin $J_2$ Is a Ligand for the Adipocyte Determination Factor PPARγ", Cell vol. 83:803–812 (1995).

de Wet et al, "Firefly Luciferase Gene: Structure and Expression in Mammalian Cells", Mol. Cell Biol. vol. 7, No. 2, 725–737 (Feb. 1987).

Heyman et al, "9–Cis Retinoic Acid Is a High Affinity Ligand for the Retinoid X Receptor", Cell vol. 68: 397–406 (1992).

Corey et al, "Useful Procedures for the Oxidation of Alcohols Involving Pyridinium Dichromate in Aprotic Media" Tet. Lett., No. 5, 399–402, 1979.

Omura et al, "Oxidation of Alcohols by "Activated" Dimethyl Sulfoxide. A Preparative, Steric and Mechanistic Study", Tetrahedron vol. 34, 1651–1660, (1978).

| | | | |
|---|---|---|---|
| 1 |  STRUCTURE<br>STEREOCHEMISTRY<br>AGN 190205 LG030002 |  STRUCTURE<br>STEREOCHEMISTRY<br>AGN 191193 LG030050 | 2 |
| 3 |  STRUCTURE<br>STEREOCHEMISTRY<br>AGN 191859 LG030012 |  STRUCTURE<br>STEREOCHEMISTRY<br>AGN 191860 LG030013 | 4 |
| 5 |  STRUCTURE<br>STEREOCHEMISTRY<br>AGN 191557 LG030035 |  STRUCTURE<br>STEREOCHEMISTRY<br>AGN 191662 LG030723 | 6 |
| 7 |  STRUCTURE<br>STEREOCHEMISTRY<br>AGN 191673 LG030092 |  STRUCTURE<br>STEREOCHEMISTRY<br>AGN 191872 | 8 |

9

STRUCTURE

STEREOCHEMISTRY

AGN 191936  LG030127

10

STRUCTURE

STEREOCHEMISTRY

AGN 192337  LG030155

11

STRUCTURE

STEREOCHEMISTRY

AGN 191547  LG030033

12

STRUCTURE

STEREOCHEMISTRY

AGN 191514

13

STRUCTURE

STEREOCHEMISTRY

AGN 191481  LG030032

14

STRUCTURE

STEREOCHEMISTRY

AGN 191180

15

STRUCTURE

STEREOCHEMISTRY

AGN 192776

16

STRUCTURE

STEREOCHEMISTRY

AGN 192856  LG030278

SEQUENCE LISTING

```
<160> NUMBER OF SEQ ID NOS: 10

<210> SEQ ID NO 1
<211> LENGTH: 469
<212> TYPE: PRT
<213> ORGANISM: Rattus norvegicus

<400> SEQUENCE: 1

Met Asn Leu Ile Gly Pro Ser His Leu Gln Ala Thr Asp Glu Phe Ala
1               5                   10                  15

Leu Ser Glu Asn Leu Phe Gly Val Leu Thr Glu His Ala Ala Gly Pro
            20                  25                  30

Leu Gly Gln Asn Leu Asp Leu Glu Ser Tyr Ser Pro Tyr Asn Asn Val
        35                  40                  45

Gln Phe Pro Gln Val Gln Pro Gln Ile Ser Ser Ser Ser Tyr Tyr Ser
    50                  55                  60

Asn Leu Gly Phe Tyr Pro Gln Gln Pro Glu Asp Trp Tyr Ser Pro Gly
65                  70                  75                  80

Leu Tyr Glu Leu Arg Arg Met Pro Thr Glu Ser Val Tyr Gln Gly Glu
                85                  90                  95

Thr Glu Val Ser Glu Met Pro Val Thr Lys Lys Pro Arg Met Ala Ala
            100                 105                 110

Ser Ser Ala Gly Arg Ile Lys Gly Asp Glu Leu Cys Val Val Cys Gly
        115                 120                 125

Asp Arg Ala Ser Gly Tyr His Tyr Asn Ala Leu Thr Cys Glu Gly Cys
    130                 135                 140

Lys Gly Phe Phe Arg Arg Ser Ile Thr Lys Asn Ala Val Tyr Lys Cys
145                 150                 155                 160

Lys Asn Gly Gly Asn Cys Val Met Asp Met Tyr Met Arg Arg Lys Cys
                165                 170                 175

Gln Asp Cys Arg Leu Arg Lys Cys Arg Glu Met Gly Met Leu Ala Glu
```

```
                    180                 185                 190
Cys Leu Leu Thr Glu Ile Gln Cys Lys Ser Lys Arg Leu Arg Lys Asn
                195                 200                 205
Val Lys Gln His Ala Asp Gln Thr Val Asn Glu Asp Ser Glu Gly Arg
            210                 215                 220
Asp Leu Arg Gln Val Thr Ser Thr Lys Leu Cys Arg Glu Lys Thr
225                 230                 235                 240
Glu Leu Thr Val Asp Gln Gln Thr Leu Leu Asp Tyr Ile Met Asp Ser
                245                 250                 255
Tyr Ser Lys Gln Arg Met Pro Gln Glu Ile Thr Asn Lys Ile Leu Lys
                260                 265                 270
Glu Glu Phe Ser Ala Glu Glu Asn Phe Leu Ile Leu Thr Glu Met Ala
            275                 280                 285
Thr Ser His Val Gln Ile Leu Val Glu Phe Thr Lys Arg Leu Pro Gly
            290                 295                 300
Phe Gln Thr Leu Asp His Glu Asp Gln Ile Ala Leu Leu Lys Gly Ser
305                 310                 315                 320
Ala Val Glu Ala Met Phe Leu Arg Ser Ala Glu Ile Phe Asn Lys Lys
                325                 330                 335
Leu Pro Ala Gly His Ala Asp Leu Leu Glu Glu Arg Ile Arg Lys Ser
            340                 345                 350
Gly Ile Ser Asp Glu Tyr Ile Thr Pro Met Phe Ser Phe Tyr Lys Ser
            355                 360                 365
Val Gly Glu Leu Lys Met Thr Gln Glu Glu Tyr Ala Leu Leu Thr Ala
            370                 375                 380
Ile Val Ile Leu Ser Pro Asp Arg Gln Tyr Ile Lys Asp Arg Glu Ala
385                 390                 395                 400
Val Glu Lys Leu Gln Glu Pro Leu Leu Asp Val Leu Gln Lys Leu Cys
                405                 410                 415
Lys Ile Tyr Gln Pro Glu Asn Pro Gln His Phe Ala Cys Leu Leu Gly
            420                 425                 430
Arg Leu Thr Glu Leu Arg Thr Phe Asn His His Ala Glu Met Leu
            435                 440                 445
Met Ser Trp Arg Val Asn Asp His Lys Phe Thr Pro Leu Leu Cys Glu
        450                 455                 460
Ile Trp Asp Val Gln
465

<210> SEQ ID NO 2
<211> LENGTH: 484
<212> TYPE: PRT
<213> ORGANISM: Mus musculus

<400> SEQUENCE: 2

Met Val Met Gln Phe Gln Gly Leu Glu Asn Pro Ile Gln Ile Ser Leu
  1               5                  10                  15
His His Ser His Arg Leu Ser Gly Phe Val Pro Asp Gly Met Ser Val
                20                  25                  30
Lys Pro Ala Lys Gly Met Leu Thr Glu His Ala Ala Gly Pro Leu Gly
            35                  40                  45
Gln Asn Leu Asp Leu Glu Ser Tyr Ser Pro Tyr Asn Asn Val Pro Phe
        50                  55                  60
Pro Gln Val Gln Pro Gln Ile Ser Ser Ser Ser Tyr Tyr Ser Asn Leu
65                  70                  75                  80
```

```
Gly Phe Tyr Pro Gln Gln Pro Glu Asp Trp Tyr Ser Pro Gly Ile Tyr
                85                  90                  95
Glu Leu Arg Arg Met Pro Ala Glu Thr Gly Tyr Gln Gly Glu Thr Glu
            100                 105                 110
Val Ser Glu Met Pro Val Thr Lys Lys Pro Arg Met Ala Ala Ala Ser
        115                 120                 125
Ala Gly Arg Ile Lys Gly Asp Glu Leu Cys Val Val Cys Gly Asp Arg
130                 135                 140
Ala Ser Gly Tyr His Tyr Asn Ala Leu Thr Cys Glu Gly Cys Lys Gly
145                 150                 155                 160
Phe Phe Arg Arg Ser Ile Thr Lys Asn Ala Val Tyr Lys Cys Lys Asn
                165                 170                 175
Gly Gly Asn Cys Val Met Asp Met Tyr Met Arg Arg Lys Cys Gln Glu
            180                 185                 190
Cys Arg Leu Arg Lys Cys Arg Glu Met Gly Met Leu Ala Glu Cys Leu
        195                 200                 205
Leu Thr Glu Ile Gln Cys Lys Ser Lys Arg Leu Arg Lys Asn Val Lys
    210                 215                 220
Gln His Ala Asp Gln Thr Val Asn Glu Asp Ser Glu Gly Arg Asp
225                 230                 235                 240
Leu Arg Gln Val Thr Ser Thr Thr Lys Phe Cys Arg Glu Lys Thr Glu
                245                 250                 255
Leu Thr Ala Asp Gln Gln Thr Leu Leu Asp Tyr Ile Met Asp Ser Tyr
            260                 265                 270
Asn Lys Gln Arg Met Pro Gln Glu Ile Thr Asn Lys Ile Leu Lys Glu
        275                 280                 285
Glu Phe Ser Ala Glu Glu Asn Phe Leu Ile Leu Thr Glu Met Ala Thr
    290                 295                 300
Ser His Val Gln Ile Leu Val Glu Phe Thr Lys Lys Leu Pro Gly Phe
305                 310                 315                 320
Gln Thr Leu Asp His Glu Asp Gln Ile Ala Leu Leu Lys Gly Ser Ala
                325                 330                 335
Val Glu Ala Met Phe Leu Arg Ser Ala Glu Ile Phe Asn Lys Lys Leu
            340                 345                 350
Pro Ala Gly His Ala Asp Leu Leu Glu Glu Arg Ile Arg Lys Ser Gly
        355                 360                 365
Ile Ser Asp Glu Tyr Ile Thr Pro Met Phe Ser Phe Tyr Lys Ser Val
    370                 375                 380
Gly Glu Leu Lys Met Thr Gln Glu Glu Tyr Ala Leu Leu Thr Ala Ile
385                 390                 395                 400
Val Ile Leu Ser Pro Asp Arg Gln Tyr Ile Lys Asp Arg Glu Ala Val
                405                 410                 415
Glu Lys Leu Gln Glu Pro Leu Leu Asp Val Leu Gln Lys Leu Cys Lys
            420                 425                 430
Met Tyr Gln Pro Glu Asn Pro Gln His Phe Ala Cys Leu Leu Gly Arg
        435                 440                 445
Leu Thr Glu Leu Arg Thr Phe Asn His His Ala Glu Met Leu Met
    450                 455                 460
Ser Trp Arg Val Asn Asp His Lys Phe Thr Pro Leu Leu Cys Glu Ile
465                 470                 475                 480
Trp Asp Val Gln

<210> SEQ ID NO 3
```

```
<211> LENGTH: 472
<212> TYPE: PRT
<213> ORGANISM: Homo sapiens

<400> SEQUENCE: 3

Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
            20                  25                  30

Val Ala Gly Pro Leu Gly Gln Asn Leu Glu Val Glu Pro Tyr Ser Gln
        35                  40                  45

Tyr Ser Asn Val Gln Phe Pro Gln Val Gln Pro Gln Ile Ser Ser Ser
    50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
    130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
        195                 200                 205

Arg Lys Asn Val Lys Gln His Ala Asp Gln Thr Val Asn Glu Asp Ser
    210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
            260                 265                 270

Ile Leu Lys Glu Glu Phe Ser Ala Glu Glu Asn Phe Leu Ile Leu Thr
        275                 280                 285

Glu Met Ala Thr Asn His Val Gln Val Leu Val Glu Phe Thr Lys Lys
    290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
    370                 375                 380

Leu Thr Ala Ile Val Ile Leu Ser Pro Asp Arg Gln Tyr Ile Lys Asp
```

-continued

```
              385                 390                 395                 400
Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
    450                 455                 460

Leu Cys Glu Ile Trp Asp Val Gln
465                 470

<210> SEQ ID NO 4
<211> LENGTH: 462
<212> TYPE: PRT
<213> ORGANISM: Homo sapiens

<400> SEQUENCE: 4

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285
```

```
                -continued

Phe Ser Glu Leu Pro Leu Asp Asp Gln Val Ile Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
                355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
                420                 425                 430

Leu Glu His Leu Phe Phe Phe Lys Leu Ile Gly Asp Thr Pro Ile Asp
            435                 440                 445

Thr Phe Leu Met Glu Met Leu Glu Ala Pro His Gln Met Thr
    450                 455                 460

<210> SEQ ID NO 5
<211> LENGTH: 147
<212> TYPE: PRT
<213> ORGANISM: Saccharomyces cerevisiae

<400> SEQUENCE: 5

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
                35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
    130                 135                 140

Thr Val Ser
145

<210> SEQ ID NO 6
<211> LENGTH: 39
<212> TYPE: DNA
<213> ORGANISM: Artificial Sequence
<220> FEATURE:
<223> OTHER INFORMATION: Junction between yeast GAL-4 DBD and human RXR
      alpha LBD coding regions in GAL-L-RXR
```

```
<400> SEQUENCE: 6
gtatcgccgg aattcggtac cgtcgaggcc gtgcaggag                           39

<210> SEQ ID NO 7
<211> LENGTH: 56
<212> TYPE: DNA
<213> ORGANISM: Artificial Sequence
<220> FEATURE:
<223> OTHER INFORMATION: Junction between yeast GAL-4 DBD and rat RXR
      alpha LBD coding regions in GAL-L-RXR

<400> SEQUENCE: 7
gtatcgccgg aattcgggct aaggaagtgc agagagatgg gaatgttggc tgaatg       56

<210> SEQ ID NO 8
<211> LENGTH: 9
<212> TYPE: PRT
<213> ORGANISM: Artificial Sequence
<220> FEATURE:
<223> OTHER INFORMATION: SV40 nuclear localization sequence

<400> SEQUENCE: 8

Ala Pro Lys Lys Lys Arg Lys Val Gly
 1               5

<210> SEQ ID NO 9
<211> LENGTH: 360
<212> TYPE: DNA
<213> ORGANISM: Artificial Sequence
<220> FEATURE:
<223> OTHER INFORMATION: Promoter region of plasmid TK-luc

<400> SEQUENCE: 9
ggttttccca gtcacgacgt tgtaaaacga cggccagtgc caagcttgca tgcctgcagg    60
tcgactctag aggatccggc cccgcccagc gtcttgtcat tggcgaattc gaacacgcag   120
atgcagtcgg ggcggcgcgg tcccaggtcc acttcgcata ttaaggtgac gcgtgtggcc   180
tcgaacaccg agcgaccctg cagcgacccg cttaacagcg tcaacagcgt gccgcagatc   240
tctcgagtcc ggtactgttg gtaaaatgga agacgccaaa aacataaaga aaggcccggc   300
gccattctat cctctagagg atggaaccgc tggagagcaa ctgcataagg ctatgaagag   360

<210> SEQ ID NO 10
<211> LENGTH: 24
<212> TYPE: DNA
<213> ORGANISM: Artificial Sequence
<220> FEATURE:
<223> OTHER INFORMATION: Consensus S. cerevisiae UAGg response element

<400> SEQUENCE: 10
cgacggagta ctgtcctccg agct                                          24
```

METHODS FOR MODULATING FXR RECEPTOR ACTIVITY

This application claims priority under 35 USC 119(e) to Provisional Patent Application Ser. No. 60/138,968, filed Jun. 11, 1999, hereby incorporated by reference herein.

FIELD OF THE INVENTION

The present invention is relevant to the fields of human and veterinary medicine, physiology and biochemistry, particularly in the regulation of lipid metabolism and catabolism and cholesterol synthesis and breakdown.

BACKGROUND OF THE INVENTION

A vast array of specific metabolic, developmental, and catabolic processes appear to be directly or indirectly regulated in vivo by comparatively small molecules such as steroids, retinoids and thyroid hormones. The mechanism whereby a single such compound can contribute to the regulation of numerous different cellular events was the subject of much speculation until relatively recently, when it was discovered that these compounds each share the ability to bind to transcriptionally active proteinaceous receptors. These protein receptors, in turn, are able to bind specific cis-acting nucleic acid regulatory sequence regions, termed response elements or RE's, located upstream of the coding sequence of certain genes and to activate the transcription of these genes. Thus, the proteinaceous receptors can serve as specific, ligand-dependent regulators of gene transcription and expression.

The amino acid sequences of these various receptors were quickly found to share regions of homology, thus making each such receptor a member of a family of ligand-modulated receptor molecules. This family has been termed the steroid superfamily of nuclear hormone receptors; nuclear, because the receptors are usually found in high concentration in the nucleus of the cell.

Further study of the structural and functional relationship between the nuclear hormone receptors has shown certain characteristics in common between them in addition to sequence homology. See e.g., Evans et al. *Science* 240:889–895 (1988). As stated above, the nuclear hormone receptors are able to bind to cis-acting regulatory elements present in the promoters of the target genes. The glucocorticoid, estrogen, androgen, progestin, and mineralcorticoid receptors have been found to bind as homodimers to specific response elements organized as inverted repeats.

Another class of nuclear hormone receptors, which includes the retinoid receptor RAR (retinoic acid receptor), the thyroid receptor, the vitamin D receptor, the peroxisome proliferator receptor, and the insect ecdysone receptor bind their response element as a heterodimer in conjunction with the retinoid X receptor (RXR), which in turn is positively activated by 9-cis retinoic acid. See Mangelsdorf, et al., *The Retinoid Receptors* in *The Retinoids: Biology, Chemistry and Medicine* Ch.8 (Sporn et al., eds. 2d ed., Raven Press Ltd. 1994); Nagpal and Chandraratna, *Current Pharm. Design* 2:295–316 (1996), which are both incorporated by reference herein. The retinoid receptors RAR and RXR, like many nuclear receptors, exist as a number of subtypes (RARα, RARβ, RARγ, and RXRα, RXRβ, and RXRγ). Additionally, each subtype may exist in different isoforms.

While the nuclear hormone receptors referenced above have all been shown to have specific ligand partners, nucleic acid and amino acid sequencing experiments and sequence alignment and comparison have revealed a class of protein molecules retaining significant sequence homology and structural similarity to the nuclear hormone receptor superfamily, but for which no corresponding ligand has yet been discovered. In fact, some of these "receptors" have been discovered to require no ligand binding to exhibit transcriptional activity. These receptors have been collectively termed "orphan" receptors.

Products of intermediate metabolism are known transcriptional regulators in prokaryotes and lower eukaryotes such as yeast; thus there has been speculation that such metabolites may also serve this function in higher organisms, perhaps through interaction with the nuclear hormone receptors.

Farnesol is an isoprenoid involved in the mevalonate biosynthetic pathway, which leads to the synthesis of cholesterol, bile acids, porphyrin, dolichol, ubiquinone, carotenoids, retinoids, vitamin D, seroid hormones, and farnesylated proteins. Farnesyl pyrophosphate, a derivative of farnesol, is the last common intermediate in the mevalonate biosynthetic pathway.

Foreman et al., *Cell* 81:687–693 (1995) have demonstrated that an orphan receptor, now termed farnesoid X-activated receptor (FXR), is activated by farnesol and related molecules. This reference is hereby incorporated by reference herein. FXR is expressed in the liver, gut, adrenal gland, and kidney.

The amino acid sequence of FXR reveals a conserved DNA-binding domain (DBD) and ligand-binding domain (LBD). The LBD comprises subdomains responsible for ligand binding, receptor dimerization, and transactivation. Additionally, cells expressing chimeric proteins that contain the LBD of FXR fused to the DBD of the yeast GAL4 transcription activator did not transcribe a reporter gene containing a GAL4 response element unless the FXR construct was coexpressed with another protein comprising the dimerization and ligand binding subdomains of RXR. These data suggested that FXR and RXR interact to form a transcriptionally active dimer. No interaction was seen between FXR and any other nuclear hormone receptors that were tested. Id.

Among the nuclear hormone receptors amino acid sequence homology to FXR is high in the insect ecdysone receptor (EcR), which dimerizes with an RXR homolog. When dimerized with RXRα, FXR was shown to specifically bind hsp27, an EcR response element, however, binding was not seen when FXR was expressed alone. FXR and RXR bind to certain sequences as a heterodimer.

The FXR-RXRα complex was found to be activated by juvenile hormone III (JH III); incubation of cells transfected with RXR and FXR. The cells were also transfected with a reporter plasmid containing 5 copies of the hsp27 response element within a portion of the mouse mammary tumor virus (MTV) promoter; the promoter was positioned upstream of the firefly luciferase gene. Activation of this gene results in the expression of luciferase, which is easily quantifiable as a measure of transactivation activity. Other potential ligands, including selected steriods, and eicosanoids were found to have no effect in this system. JH III failed to activate other nuclear hormone receptors, and does not activate either FXR or RXR alone. Forman et al., *Cell* 81:687–693 (1995).

JH III is a derivative of farnesyl pyrophosphate. Other farnesyl derivatives have been tested for the ability to activate the FXR-RXR complex. Farnesol was demonstrated to strongly activate the heterodimer. Other derivatives such as farnesal, farnesyl acetate, farnesoic acid and geranylgeraniol activated the FXR-RXR complex somewhat less strongly; the farnesyl metabolites geraniol, squalene and cholesterol did not activate FXR-RXR. Id.

Cholesterol synthesis is closely regulated by modulation of the levels of 3-hydroxy-3-methylglutaryl-coenzyme A reductase(HMG-CoA), which regulates the conversion of 3-hydroxy-3-methylglutaryl-coenzyme A to mevalonate. Through a series of phosphorylations and a decarboxylation reaction, mevalonate is converted into 3-isopentenyl pyrophosphoric acid, which isomerizes to 3,3-dimethylallyl pyrophosphoric acid. An enzyme-mediated condensation reaction between the 5 carbon isoprenyl compounds 3-isopentenyl pyrophosphoric acid and 3,3-dimethylallyl pyrophosphoric acid results in the formation of the 10 carbon diisoprenyl compound geranyl pyrophosphoric acid. This, in turn, reacts with another molecule of 3-isopentenyl pyrophosphoric acid to form the 15 carbon compound farnesyl pyrophosphate. Two molecules of this latter compound react to form the 30 carbon molecule presqualine pyrophosphate, which is dephosphorylated to form squaline. Squaline is then cyclized to form cholesterol. Thus, HMG-CoA reductase mediates the initial formation of the isoprene units that are subsequently assembled in series and cyclized to form cholesterol.

The levels of HMG-CoA reductase are governed in part by controlling the gene transcription, translation, and by degradation of the enzyme. Farnesol has recently been shown to be involved in the regulation of HMG-CoA reductase degradation. Evidence exists for the synergistic promotion of HMG-CoA reductase degradation by farnesol and a sterol component, such as 25-hydroxycholesterol. See e.g., Meigs et al., *J. Biol. Chem.* 271:7916–7922 (1996), hereby incorporated by reference herein.

Cholesterol is the precursor of various compounds such as sterols, bile acids such as cholic acid, and the steroid hormones such as testosterone and progesterone. All these compounds retain the basic cholesterol nucleus. The more polar bile acids are formed in the liver and secreted into the small intestine, where they aid in the absorption of lipids. The formation of bile acids from cholesterol is therefore an important degradation pathway for cholesterol, and is a key determinant of the steady-state concentration of cholesterol in the body.

The rate-limiting enzyme in the formation of bile acids from cholesterol is cholesterol 7α-hydrolase (Cyp7a). For some time it has been known that bile acids act in a negative feedback loop to limit their own production via this pathway, but the means by which this is accomplished has remained elusive. Recently, there has been evidence that Cyp7a synthesis and expression is inhibited by bile acids. Chiang, *Front. Biosci.* 3:D176-93 (1998) hereby incorporated by reference herein.

Despite the fact that cholesterol is essential for the synthesis of cell membranes and various hormones and other small molecules, raised levels of cholesterol, particularly in the form of low density lipoprotein (LDL), have been strongly linked to arteriosclerosis and other cardiovascular diseases. Additionally, maintenance of appropriate bile acid concentrations is important in regulating lipid metabolism, and may be useful in the prevention of colon cancer and gallstone formation.

Among currently available drugs for the treatment of hypercholesterolemia are ion exchange media such as colestipol and cholestyramine. These drugs function by sequestering bile acids in the gut; the bile acids are then excreted in the feces. Because the intestine does not reabsorb the sequestered bile acids, the bile acids are no longer available to inhibit the formation of bile acids by cholesterol degradation. As a result, bile acid synthesis is "depressed" with the result that the steady-state concentration of cholesterol is lowered.

Unfortunately, these ion exchange drugs have been associated with an increased incidence of intestinal tumors in rodents. Additionally, since the drugs are highly charged, they are capable of adsorbing other compounds, such as ingested drugs, naturally occurring hormones, regulatory factors and the like.

Recently a poster displayed by Neisor, Flach, Weinberger & Bentzen at an AACR conference on Nuclear Receptors in Palm Springs, Calif. held on Jan. 8–11, 1999 discussed the ability of certain 1,1-biphosphonate esters to activate FXR and to lower plasma cholesterol levels in mammals. This poster abstract is incorporated by reference herein.

Thus, there remains a need in the art for methods of modulating the steady-state concentration of cholesterol and/or bile acids. Such methods preferably do not significantly interact with other therapeutic agents, and function to help promote the breakdown or formation of cholesterol in a more direct fashion.

SUMMARY OF THE INVENTION

Figure 1:
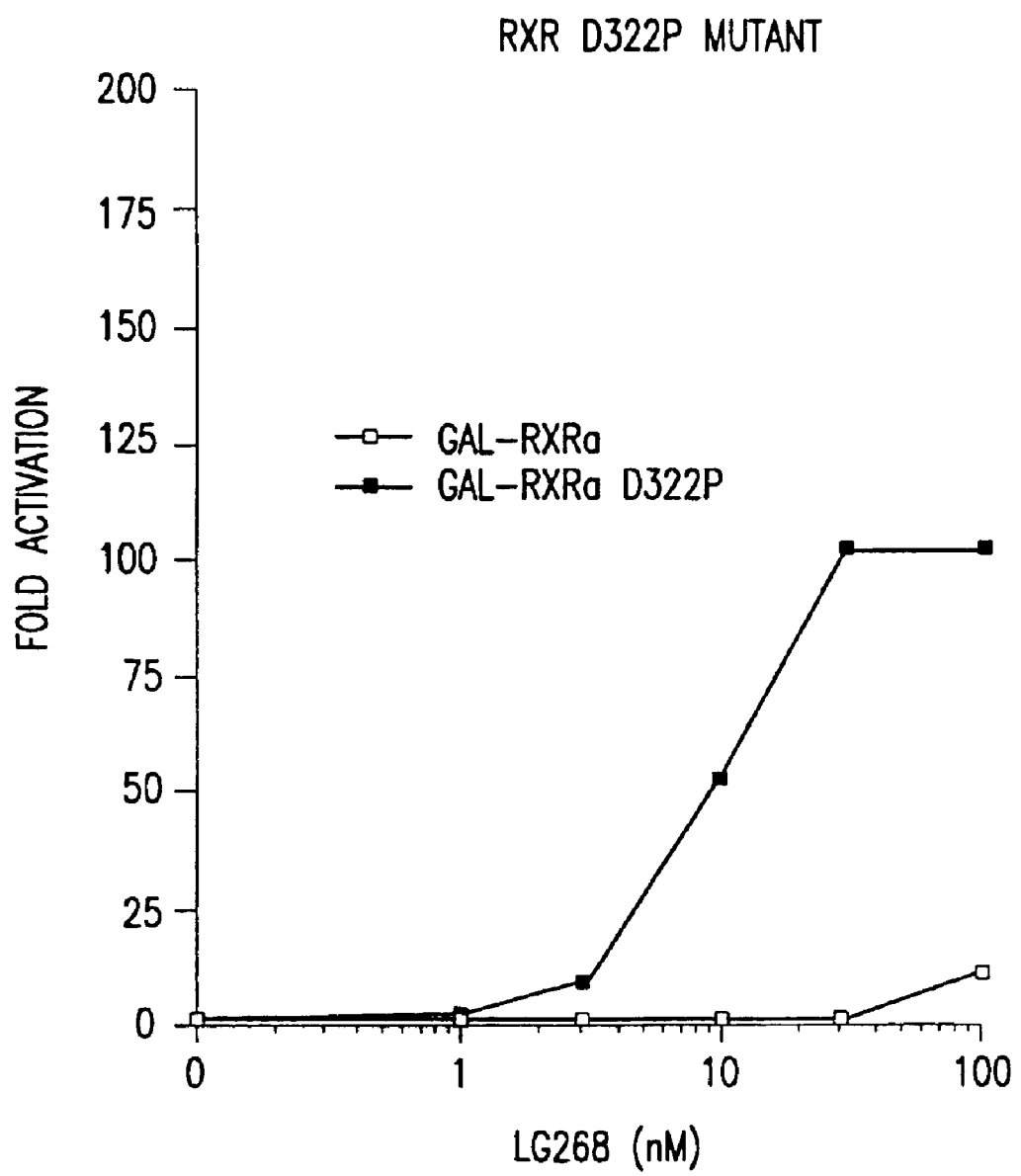
FIG. 1 is a dose-response curve plotting the ability of the GAL-RXR and GAL-RXR$_m$ proteins to transcriptionally activate UAS$_G$-Tk-Luc in the presence of an RXR agonist, LG 268.

The present invention is directed to methods for modulating the transcriptional activity of FXR through the use of synthetic FXR ligands. In a preferred embodiment the compositions are ligands of FXR able to cause FXR, alone or preferably in combination with another nuclear hormone receptor such as RXR, to suppress, inhibit, or stimulate the transcription of a given target gene. In a currently most preferred embodiment, FXR is substantially inactive in its ability to modulate gene expression unless it associates with RXR. Additionally, it is preferred that the FXR ligand is not substantially active as a modulating ligand of either or both RAR and RXR receptors.

It has been discovered that, when activated by an appropriate ligand, FXR is a bile acid receptor that is able to regulate the expression of Cyp7a, thereby controlling a key step in the degradation of cholesterol. Thus, in a particularly preferred embodiment, the invention concerns methods for controlling the concentrations of cholesterol and bile acids in vivo through the use of specific FXR ligands. See Wang, et al., *Molec. Cell* 3:543–553 (May 1999), hereby incorporated by reference herein. In another embodiment, a synthetic FXR agonist may be used to increase the concentration of cholesterol within a hypocholesterolemic mammal.

Of course, ligand-dependent activities of FXR other than the regulation of Cyp7a expression can also be controlled through the use of an appropriate FXR ligand. For example, also contemplated by the present invention are methods for regulating the concentration of bile acids in a mammal. A heightened concentration of bile acids in mammals has been associated with an increased occurrence of colon cancer, thus, the use of FXR ligands to lower abnormally high bile acid concentrations may provide a therapeutic and/or prophylactic effect for this indication. Additionally, proteins other than Cyp7a are regulated by bile acids; these include Intestinal Bile Acid Binding Proteins and Cyclooxygenase 2 (both up regulated by CDCA), and sterol-27-hydroxylase, Intestinal Bile Acid Transporter, and Liver Bile Acid Transporter (these proteins are down regulated by CDCA). The methods of the present invention are therefore useful in modulating the expression of these proteins as well.

The FXR ligands of the present invention may be FXR agonists, FXR antagonists, or FXR inverse agonists. By "agonist" is meant that the ligand stimulates a ligand-dependent FXR activity above any baseline levels present in the absence of ligand. By "FXR activity" is meant the ligand-dependent direct or indirect inhibition of LXRα activity. By "antagonist" is meant that the ligand binds to FXR, and functions as a competitive or non-competitive inhibitor of FXR agonist activity. By "inverse agonist" is meant that the ligand will bind to FXR and cause the suppression of FXR activity to a level lower than seen in the absence of any FXR ligand.

Also contemplated by the present invention are methods of lowering cholesterol in a mammal, comprising treating the mammal with a pharmaceutically acceptable composition comprising an FXR antagonist or FXR inverse agonist.

In another aspect the present invention pertains to methods of stimulating or inhibiting the activity of an FXR receptor of a mammal by treating such a mammal with a pharmaceutically acceptable composition comprising a compound selected from the group consisting of Formulas 1, 2, 3 and 4

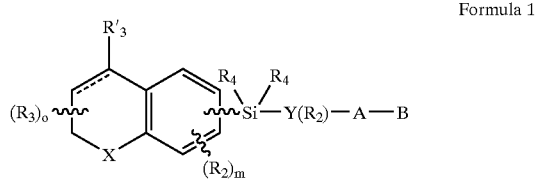

Formula 1

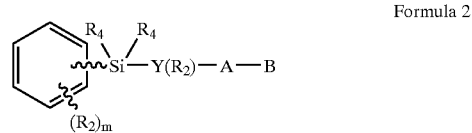

Formula 2

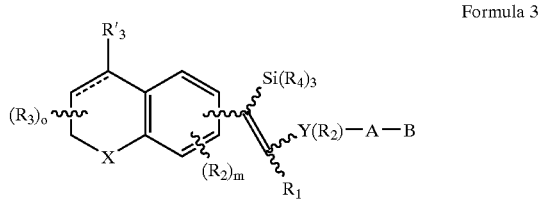

Formula 3

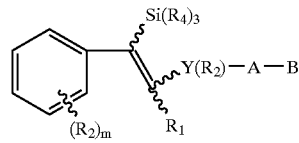

Formula 4 wherein the dashed line represents a bond or absence of a bond;

X is S, O, NR' where R' is H or alkyl of 1 to 6 carbons, or

X is $(C(R_1)_2)_n$ where $R_1$ is H or alkyl of 1 to 6 carbons, and n is an integer having the value of 0 or 1;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 12 carbons, or alkylthio of 1 to 12 carbons, benzyloxy or $C_1$–$C_{12}$ alkylbenzyloxy;

$R_3$ is hydrogen, lower alkyl of 1 to 6 carbons or F;

m is an integer having the value of 0–3 in Formulas 1 and 3; and 0–5 in Formulas 2 and 4;

o is an integer having the value of 0–4 when the dashed line represents absence of a bond, and 0–3 when the dashed line represents a bond;

$R_3'$ is hydrogen, lower alkyl of 1 to 6 carbons, F or $R_3'$ is hydrogen, lower alkyl of 1 to 6 carbons, F or $(R_{15})_r$-phenyl, $(R_{05})_r$-naphthyl, or $(R_{15})_r$— heteroaryl where the heteroaryl group has 1 to 3 heteroatoms selected from the group consisting of O, S and N, r is an integer having the values of 0–5;

$R_4$ is alkyl of 1 to 8 carbons, or phenyl;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$R_{15}$ is independently H, F, Cl, Br, I, $NO_2$, $N(R_8)_2$, $NH(R_8)$, $COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $NO_2$, $P(O)(OH)_2$, $P(O)(OH)OR_8$, $P(O)(OR_8)_2$, $SO_2OH$, $SO_2(OR_8)$, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

In a preferred embodiment of this latter aspect of the invention, a mammal suffering from hypercholesterolemia or hyperlipoproteinemia is treated with a pharmaceutically acceptable composition comprising an FXR antagonist selected from the group of such compounds. Preferably said mammal is a human.

In another preferred embodiment of the same aspect of the invention, a mammal suffering from hypocholesterolemia is treated with a pharmaceutically acceptable composition comprising an FXR agonist selected from the group of such compounds. Preferably said mammal is a human.

Other aspects and embodiments of the invention are contained in the disclosure that follows and the claims that conclude this specification.

DETAILED DESCRIPTION OF THE INVENTION

The present invention is directed to methods for modulating the activity of a mammalian FXR receptor, preferably the human FXR protein.

Such methods involve the use of compounds which will bind the FXR receptor, thereby affecting the ability of FXR to exert its biological effects, either directly or by blocking the ability of a naturally occurring ligand to exert its affects. The FXR ligands of the present invention may be FXR antagonists, FXR agonists, or FXR inverse agonists. Preferably, although not necessarily, the FXR ligands have substantially no activity at the retinoid nuclear receptors, RAR and RXR. In another embodiment, the FXR ligand may be a bi-specific compound able to bind and modulate both RXR and FXR.

Also included within the scope of the invention are aspects directed to methods for lowering the plasma concentration of cholesterol in a mammal, comprising treating the mammal with a pharmaceutically acceptable composition comprising an FXR antagonist or FXR inverse agonist.

Also included are aspects of the invention directed to methods for increasing the plasma concentration of cholesterol in a mammal pathologically deficient in cholesterol through the use of an FXR agonist.

Another aspect of the invention concerns methods for lowering the concentration of bile acids in a mammal, comprising the use of an FXR agonist in a pharmacologically acceptable carrier. Alternatively, in another aspect of the invention an FXR antagonist or FXR inverse agonist is used to increase the synthesis of bile acids in a patient deficient in bile acid synthesis.

While not wishing to be bound by theory, the Applicants believe that the FXR receptor, when bound by an FXR agonist, functions to inhibit the transcription of the oxysterol receptor LXRα, which in turn activates transcription of Cyp7a. Repression of transcription of this key enzyme in the biosynthesis of bile acids therefore results in a lower concentration of bile acids within the body; high bile acid concentrations have been associated with a heightened risk of colon cancer.

As an aid in the further understanding of this invention, Applicants offer the following Examples, which are intended to illustrate the invention, but not to limit the scope of the claims.

Materials and Methods

All mammalian expression vectors were derivatives of the bacterial/mammalian shuttle vector pCMX, an expression vector containing the cytomegalovirus (CMV) promoter/enhancer, followed by a bacteriophage T7 promoter for transcription of the cloned gene in vitro. Plasmid pCMX also contains the SV40 small t intron/poly adenylation signal sequence, polyoma virus enhancer/origin and the SV40 enhancer/origin of plasmid CDM8 (see Seed, *Nature* 329:840–842 (1987), hereby incorporated by reference herein) cloned into the large to Pvu II fragment of pUC19. PUC19 is a commonly used cloning vector available from New England Biolabs, Inc. This Pvu II fragment contains a Col E1 origin of replication and an ampicillin resistence gene for plasmid selection, but lacks the pUC19 polylinker cloning site. To create a new polylinker site, a synthetic polylinker comprising the following restriction sites: 5'-KpnI, EcoRV, BamHI, MscI, NheI-3' followed by a translational termination sequence inserted in all three reading frames. See Umesono et al., *Cell* 65:1255–1266 (1991), hereby incorporated by reference herein.

The nucleic acid regions encoding the following full-length proteins were cloned into pCMX. The sequences of these genes and/or their corresponding polypeptides have the indicated GenBank accession numbers: rat FXR (accession number U 18374); mouse FXR (accession number U 09416); human FXR (accession number NM 005123); and human RXRα (accession number X 52773). The GenBank information corresponding to these accession numbers is hereby incorporated by reference herein in its entirety. The rat FXR amino acid sequence, mouse FXR amino acid sequence, and human FXR amino acid sequence are provided herein as SEQ ID NO: 1, SEQ ID NO: 2, and SEQ ID NO: 3, respectively. The human RXRα amino acid sequence is provided herein as SEQ ID NO:4.

GAL4 fusion proteins were constructed using standard molecular biological methods (see e.g., Sambrook et al., *Molecular Cloning: A Laboratory Manual* (2d ed. Cold Spring Harbor Laboratory Press 1989), incorporated by reference herein in its entirety) by inserting a nucleotide sequence encoding the indicated polypeptide immediately downstream of the yeast GAL4 DNA-binding domain in plasmid pSG424, described in Sadowski et al., *Nucleic Acids Research* 17:7539, hereby incorporated by reference herein. The amino acid sequence of the yeast GAL4 DBD, hereby designated SEQ ID NO: 5, is as follows:

NH2-MKLLSIEQA CDICRLKKLK CSKEKPKCAK CLKNNWECRY SPKTKRSPLT RAHLTEVESR LERLEQLFLL IFPREDLDM ILKMDSLQD IKALLTGLF VQDNVNKDAV TDRLASVETD MPLTLRQHRI SATSS-SEESS NKGQRQLTVS-COOH

Fusion proteins were made, as indicated above, using common molecular biological techniques by creation of open nucleic acid reading frames encoding the indicated polypeptides, and cloning into the polylinker portion of pCMX.

For GAL-L-RXR, the plasmid nucleic acids encoded amino acids $Glu_{203}$ to $Thr_{462}$ of human RXRα(SEQ ID NO: 4) fused to the GAL4 sequences. The junction between the carboxyl terminal section of GAL4 and the amino terminal portion of the RXR LBD had the following structure:

```
                  EcoRI      Asp718   Sal/Xho
GTA-TCG-CCG-GAA-TTC-GGT-ACC-GTC-GAG-GCC-GTG-CAG-GAG- . . .
Val-Ser                              Glu-Ala-Val-Gln-Glu- . . .
  GAL4 ->                              203 -->hRXRa LBD
```

This junction nucleotide sequence
5'GTATCGCCGGAATTCGGTACCGTCGAG-GCCGTGCAGGAG3'
is hereby designated SEQ ID NO: 6.

For GAL-L-FXR, the plasmid nucleic acids encoded amino acids $Leu_{181}$ to $Gln_{469}$ of rat FXR (SEQ ID NO:1) fused to the GAL4 sequences. The junction between the carboxyl terminal section of GAL4 and the amino terminal portion of the FXR LBD had the following structure:

located immediately upstream (i.e., to the 5' side on the coding strand) of a nucleotide sequence encoding the human RXRα LBD ($Glu_{203}$ to $Thr_{462}$). CMX-βgal contains the *E. coli* β-galactosidase coding sequence derived from plasmid pCH110 (accession number U 02445) inserted downstream of the CMV promoter in plasmid pCMX. RXRm contains a single point mutation changing Asp-322 to Pro in the LBD of human RXRα.

```
EcoRI former
      |         KpnI/NaeI
 GTATCGCCGGAATTCGGGCTAAGGAAGTGCAGAGAGATGGGAATGTTGGCTGAATG
 ValSerProGluPheGlyLeuArgLysCysArgGluMetGlyMetLeuAlaGlu
 GAL4>|            |<---rFXRa AA 181        |<---LBD
```

This junction nucleotide sequence (from 5' to 3')
GTATCGCCGGAATTCGGGCTAAGGAAGTGCAGAGAGATGGGAATGTTGGCTGAATG
is hereby designated SEQ ID NO: 7.

RXR ligand binding domain (LBD) expression construct L-RXR contains nucleotide residues encoding the SV40 Tag nuclear localization signal sequence (from amino to carboxy ends:

APKKKRKVG (SEQ ID NO:8)

Luciferase reporter plasmids (termed TK-Luc) were constructed by placing the cDNA encoding firefly luciferase immediately downstream from the herpes virus thymidine kinase promoter (located at nucleotide residues −105 to +51) of the thymidine kinase nucleotide sequence), which is linked in turn to the various response elements. The promoter region of the TK-Luc plasmids has the following structure:

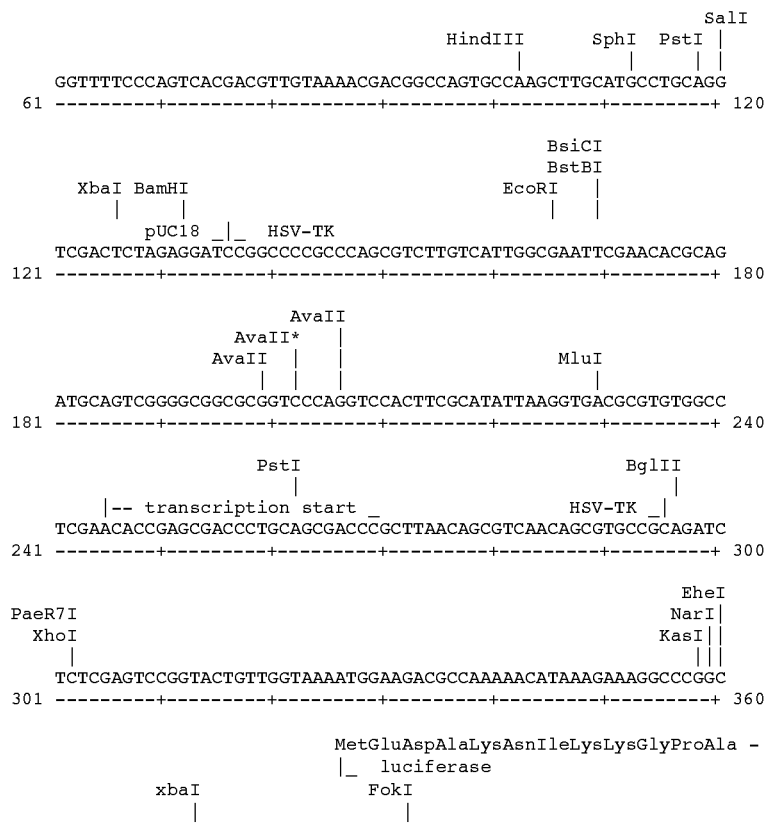

```
                             -continued
    GCCATTCTATCCTCTAGAGGATGGAACCGCTGGAGAGCAACTGCATAAGGCTATGAAGAG
361 ---------+---------+---------+---------+---------+---------+ 420
      ProPheTyrProLeuGluAspGlyThrAlaGlyGluGlnLeuHisLysAlaMetLysArg This nucleotide sequence (continuous from 5' to 3')
5'-GGTTTTCCCAGTCACGACGTTGTAAAACGACGGCCAGTGCCAAGCTTGCATGCCTGCAGG
   TCGACTCTAGAGGATCCGGCCCCGCCCAGCGTCTTGTCATTGGCGAATTCGAACACGCAG
   ATGCAGTCGGGCGGCGCGGTCCCAGGTCCACTTCGCATATTAAGGTGACGCGTGTGGCC
   TCGAACACCGAGCGACCCTGCAGCGACCCGCTTAACAGCGTCAACAGCGTGCCGCAGATC
   TCTCGAGTCCGGTACTGTTGGTAAAATGGAAGACGCCAAAAACATAAAGAAAGGCCCGGC
   GCCATTCTATCCTCTAGAGGATGGAACCGCTGGAGAGCAACTGCATAAGGCTATGAAGAG-3'
``` is designated SEQ ID NO: 9.

Response elements were inserted in plasmid TK-Luc at the unique Hind III site. The yeast GAL4 $UAS_G$ response element has the nucleotide sequence, and was inserted in 4 direct repeats

5'-CGACGGAGTACTGTCCTCCGAGCT-3' (SEQ ID NO:10)

The hsp EcRE (ecdysone response element) was inserted into the Hind III site of plasmid TK-Luc as six direct repeats of the following sequence:

5'-TGGACAAGTGCATTGAACCCTT-3' (SEQ ID NO:11)

EXAMPLE 1

Because FXR is known to bind to its response element as a heterodimer with RXR, and because the heterodimer can be activated by ligands to RXR, a mutant RXRα protein ($RXR_m$; also referred to as D322P in the Figures) was constructed containing a single point mutation ($Asp_{322}$ to Pro) in the ligand binding domain of RXR. The use of FXR-$RXR_m$ heterodimers, permits unambiguous identification of modulators of FXR activity amongst test compounds.

Thus, a reporter plasmid was constructed containing 4 copies of the GAL4 response element $UAS_G$ positioned upstream of the firefly luciferase gene, which in turn was under the control of the herpes simplex virus thymidine kinase (TK) promoter. This reporter plasmid was cotransfected into African green monkey CV-1 cells with an expression vector (pCMX, which contains the cytomegalovirus CMV promoter located upstream of the cloning site) encoding either GAL-L-RXR (comprising the LBD of RXRα from $Glu_{203}$ to $Thr_{462}$) and the DNA-binding portion (amino acids 1–147)), of the yeast GAL4 gene product, or GAL-L-RXRm (identical to GA-L-RXR but for the single $Asp_{322} \rightarrow Pro$ point mutation in the LBD of the RXR coding sequence).

Transient transfection of the CV-1 cells was performed as follows. CV-1 cells were cultured in Dulbecco's Modified Eagle's medium containing 10% resin-charcoal stripped fetal bovine serum (FBS), 50 units/ml penicillin G and 50 μg/ml streptomycin sulfate (termed DMEM-FBS). The day prior to transfection the cells were plated to 50%–80% confluence.

Cells were transiently transformed by lipofection as described in Forman et al., Cell 83:803–12 (1995), hereby incorporated by reference herein. Liposomes (N-[1-(2,3-dioleoyloxy)propyl]-N,N,N-ammonium methyl sulfate, sold by Boehringer Mannheim under the name DOTAP) were formed according to the manufacturer's instructions. The liposomes contained reporter gene constructs (300 ng/$10^5$ cells), and either the GAL-L-RXR or GAIL-L-$RXR_M$ expression vector (20–50 ng/$10^5$ cells). The cells and liposomes were incubated together for 2 hours. Liposomes were removed by aspiration, and the cells were then incubated for approximately 44 hours (±2 hours) in the presence of various concentrations of the RXR agonist LG 268 dissolved in dimethylsulfoxide (DMSO). The structure of LG 268 is as follows:

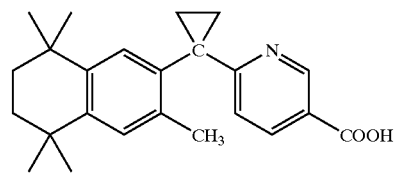

Following exposure to this compound, the cells were harvested and assayed for the presence of luciferase activity. Cells were lysed in 0.1 M KPO4 (pH 7.8), 1.0% TRITON® X-100, 1.0 mM dithiolthreitol (DTT) and 2 mM ethylene-diamine tetracetic acid (EDTA). Luciferase activity was measured by reaction of the cell lysates with luciferin in a reaction buffer comprising: 20 mM tricine, 1.07 mM $Mg(CO_3)_4$—$Mg(OH)_2$-$5H_2O$, 2.67 mM $MgSO_4$.$7H_2O$, 0.1 mM EDTA, 0.5 mM Sodium luciferin, 0.15 mg/ml Coenzyme A, 5 mM DTT, and 0.5 mM adenosine triphosphate (ATP). Resulting chemiluminescence was measured in a luminometer. See de Wet et al., Mol. Cell Biol. 7:725 (1987) (hereby incorporated by reference herein).

All compounds were assayed in triplicate. Each experiment was repeated three or more times.

Results are shown in FIG. 1. As indicated therein, introduction of the RXR $Asp_{322} \rightarrow Pro$ mutation significantly decreases ($\geq$50-fold) the ligand-dependent transactivation activity of $RXR_m$ in the presence of a known RXR agonist, LG268, compared to the transactivation ability of the unmutated ligand binding domain of GAL-L-RXR.

EXAMPLE 2

Because the FXR transctivation activity requires formation of a heterodimer with RXR, the following transactivation experiment was done to show that $RXR_m$ retains its ability to potentiate FXR activity despite a having a non-functional ligand binding domain in an assay for ligand-dependent FXR activity.

Full-length recombinant rat FXR and human RXR (or $RXR_m$) cloned into the cloning site of plasmid pCMX were cotransfected into CV-1 cells using the transient transfection method substantially as described above. Additionally, reporter plasmids were cotransfected with the expression plasmids as described above.

Luciferase reporter plasmids TK-Luc (described in Heyman et al., Cell 68:397 (1992), hereby incorporated by reference herein) were constructed by placing the firefly luciferase cDNA coding sequence in frame immediately downstream from the herpes virus thymidine kinase promoter (located at nucleotide residues −105 to +51) of the thymidine kinase nucleotide sequence). Six repeats of the EcRE response element, to which the DNA binding domain (DBD) of FXR binds, was also included upstream of the reporter gene. Further details are provided above.

Following transfection, the cells were incubated for approximately 44 hours in either bovine bile extract, 5–10 $\mu$M of the FXR test compound AGN 10 (also termed AGN 192337), or 100 nM of the RXR agonist LG 268, each dissolved in DMSO. AGN 10 has the structure:

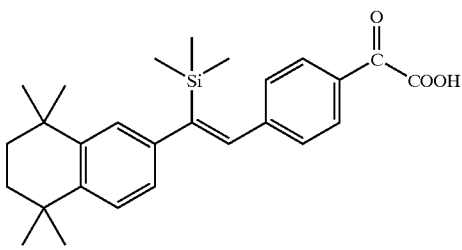

Bovine bile extract was obtained commercially from Sigma Chemicals, Inc. One gram of the bile extract was dissolved in 50 ml water and adjusted to pH 4.0. Material that was insoluble in water was extracted in 200 ml of methanol. Each of these extracts was completely dried in vacuo at 40° C., then redissolved.

Figure 2:
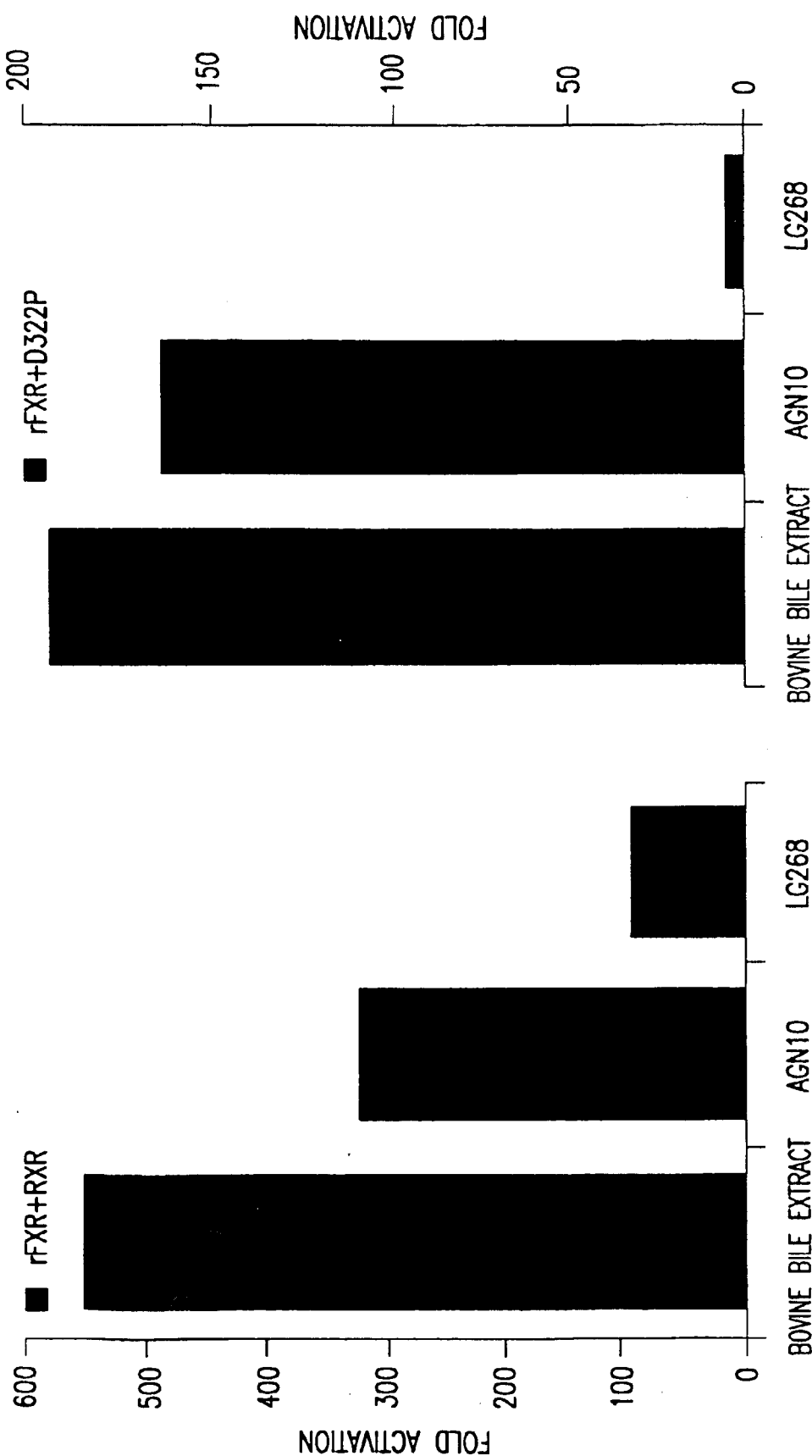
FIG. 2 is a graph comparing the ability of FXR-RXRα and FXR-RXR$_m$ heterodimers to transactivate a reporter gene in the presence of a bovine bile acid preparation, LG 268 and AGN 10.

The cells were then lysed as described above, and luciferase activity was measured as an indication of the extent of heterodimer-induced FXR transactivation activity as described above Results are shown in FIG. 2.

As can be seen, bovine bile extract has significant ability to potentiate FXR-mediated transactivation in both FXR-RXR and FXR-RXR$_m$ cotransfected cells. Also, the FXR ligand candidate AGN 10 has almost as much activity towards an FXR target (in both FXR-RXR and FXR-RXR$_m$ assays). LG 268, shown in Example 1 to have little FXR-specific activity, is able to cause transactivation of the reporter gene when exposed to a heterodimer comprising rat FXR and RXR.

By contrast, the RXR ligand LG 268 has notable activity in the FXR-RXR-transfected cells, but not in the FXR-RXRm transfected cells.

These data therefore demonstrate that FXR transactivation potentiated by FXR ligands can be distinguished from transactivation caused by RXR-specific ligand interaction with the RXR half of the active FXR-RXR heterodimer through the use of a mutated form of RXR. This Example, together with the data from Example 1, also suggests that RXRm is able to form a transactivationally active heterodimer with FXR even though RXRm is unable to bind ligand effectively. Similar results are seen using the full length human FXR protein.

EXAMPLE 3

The FXR-RXRm cotransfection methods employed in Example 2 were used to compare the FXR agonist activity of AGN 10 with the FXR activity of various bile acids, including deoxycholic acid (DCA) and chenodeoxycholic acid (CDCA) which are known to be naturally-occurring FXR ligands. See e.g., Wang et al., Molec. Cell 3:543–553 (May, 1999), hereby incorporated herein by reference.

CV-1 cells were cotransfected with mammalian expression vectors encoding full length FXR and RXRm, as well as with the luciferase reporter plasmid used in the last experiment. The cells were then incubated with one of the following agents for approximately 44 hours at a concentration of 100 nM, unless otherwise indicated: LG 268; AGN 10 (10 $\mu$M); 7-ketolithocholic acid, 3,7-diketolithocholic acid; ursodeoxycholic acid; a-muricholic acid; murocholic acid; dehydrocholic acid; taurocholic acid; cholic acid (CA); lithocholic acid (LCA); taurodeoxycholic acid; deoxycholic acid (DCA); glycochenodeoxycholic acid; taurochenodeoxycholic acid; and chenodeoxycholic acid (CDCA). All compounds were dissolved in DMSO, except glycochenodeoxycholic acid, taurochenodeoxycholic acid, taurodeoxycholic acid and taurocholic acid, which were dissolved in phosphate buffered saline (PBS). Following exposure to the compounds, the cells were washed, lysed, and the luciferase activity measured as indicated above.

Figure 3:
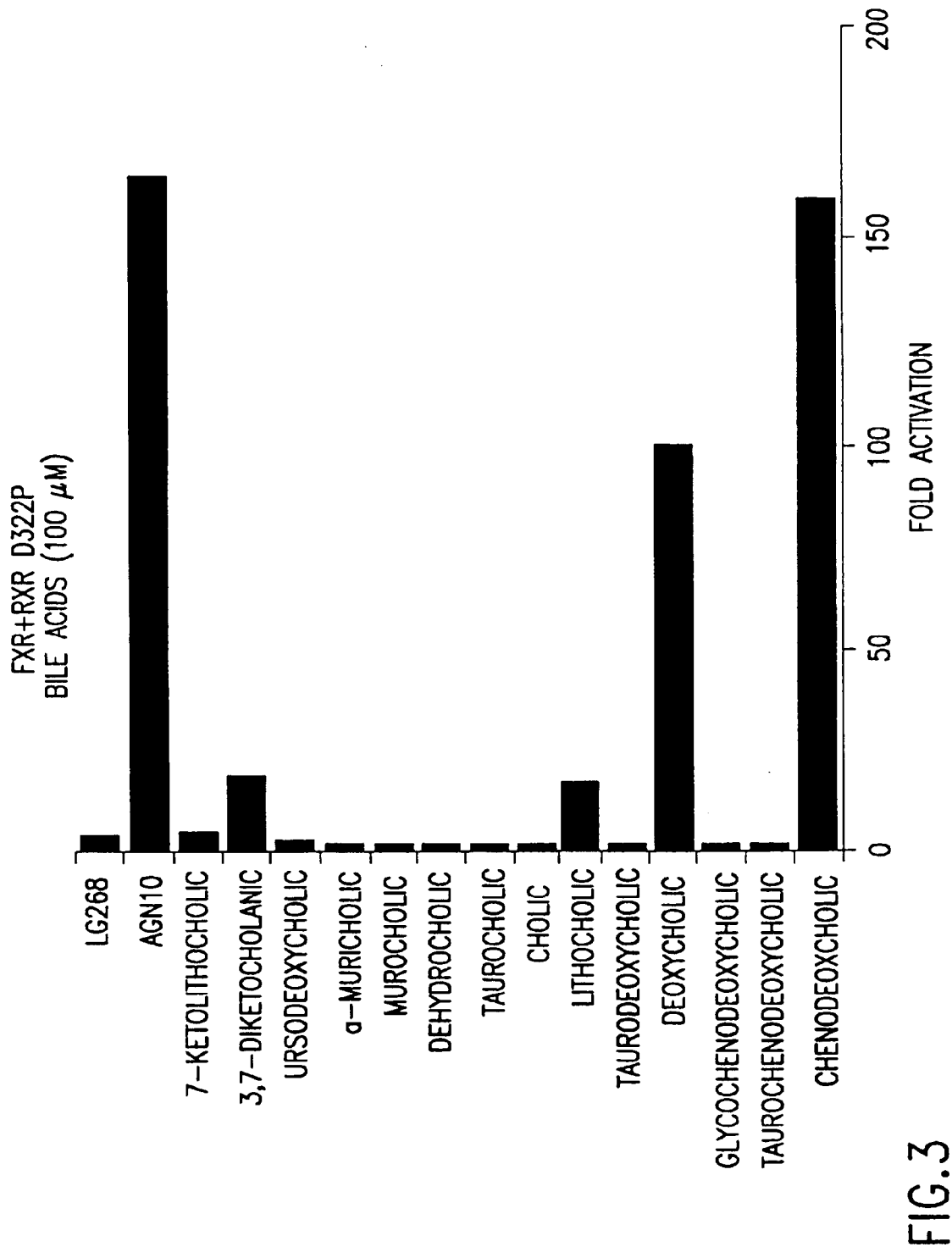
FIG. 3 is a graph comparing the ability of the FXR-RXR$_m$ heterodimer to transactivate a reporter gene in the presence of selected bile acids, LG 268 and AGN 10.

FIG. 3 indicates that, of the tested compounds, AGN 10, 7-ketolithocholic acid, 3-7-diketolithocholic acid, lithocholic acid, deoxycholic acid, and chenodeoxycholic acid have measurable FXR transactivating activity in this assay system. Of the naturally occurring bile acids only chenodeoxycholic acid (delivered at a concentration of 100 $\mu$M) showed a level of activity as great as that displayed by 10 $\mu$M AGN 10.

EXAMPLE 4

A similar experiment was performed in order to determine the FXR transactivating activity of selected compounds as a function of ligand concentration. Transient cotransfection of full length rat FXR, human RXR and the luciferase reporter plasmid was performed as above. A set of cotransfectant CV-1 cells was incubated in 1, 2, 10, and 20 $\mu$M AGN 10. Separate sets of cotransformants were given 1, 10, 20, 100, and 200 $\mu$M of either CDCA, DCA or LCA. All compounds were dissolved in DMSO. All transformant cells were permitted to incubate for approximately 44 hours with the indicated compound, then the amount of transactivation activity was measured using the luciferase assay, as indicated above.

Figure 4:
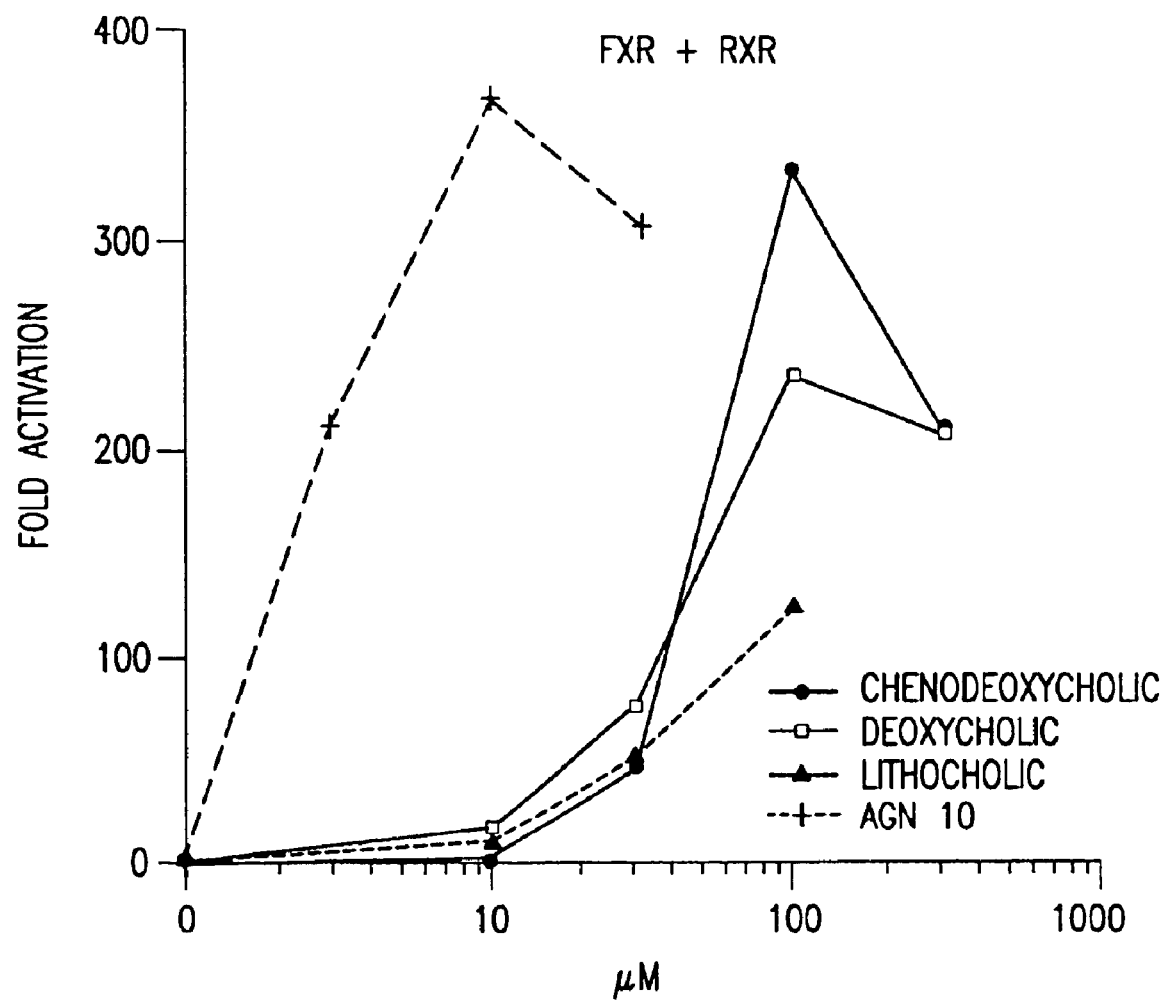
FIG. 4 shows a dose-response curve comparing the agonist activity of selected bile acids and AGN 10.
Figure 5A:
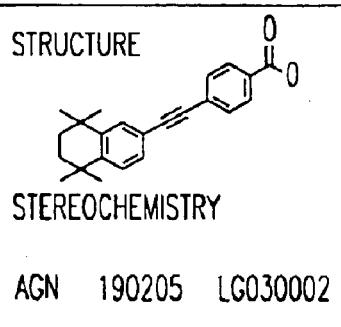
FIGS. 5a through 5d provides the structure of compounds comprising a panel of prospective FXR ligands.
Figure 5A:
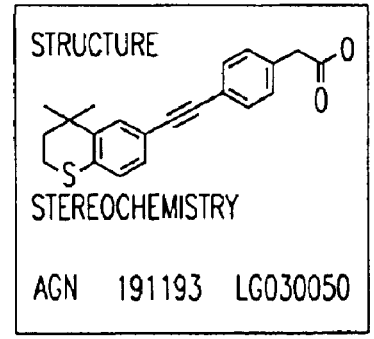
Figure 5A:
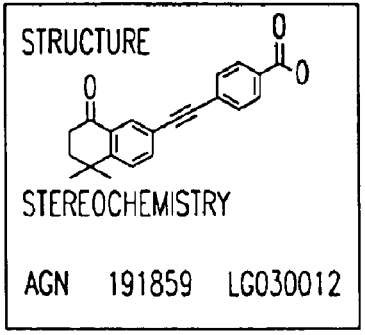
Figure 5A:
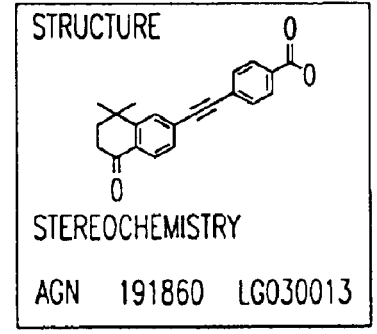
Figure 5A:
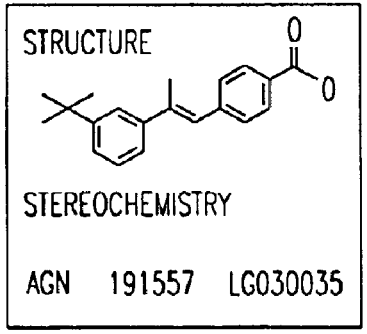
Figure 5A:
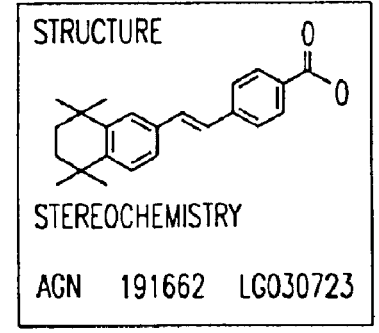
Figure 5A:
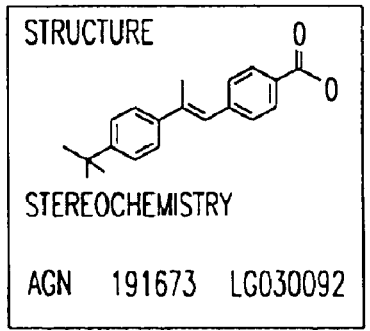
Figure 5A:
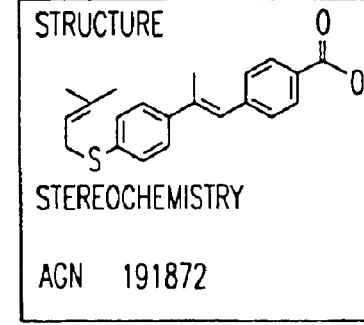
Figure 5B:
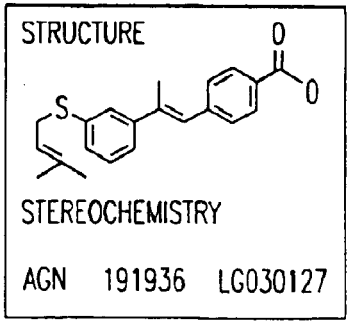
Figure 5B:
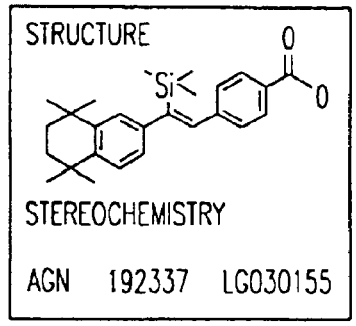
Figure 5B:
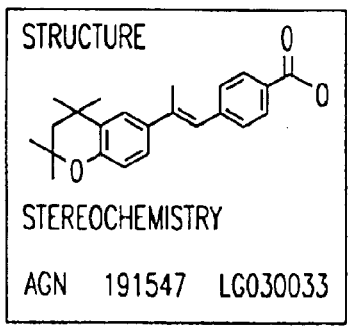
Figure 5B:
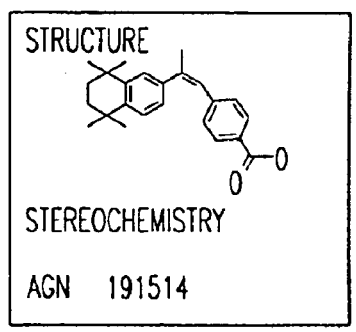
Figure 5B:
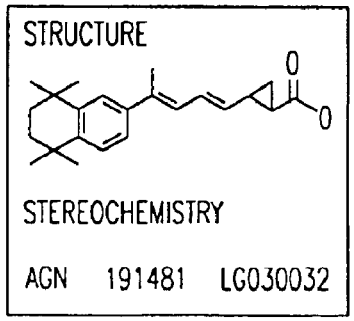
Figure 5B:
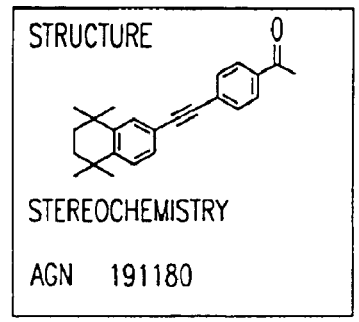
Figure 5B:
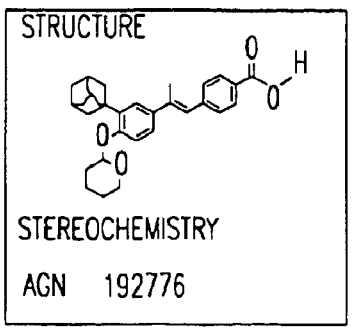
Figure 5B:
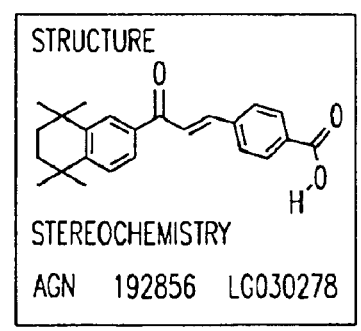
Figure 5C:
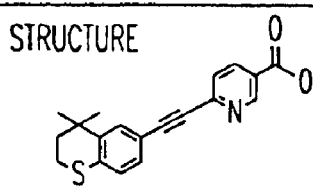
Figure 5C:
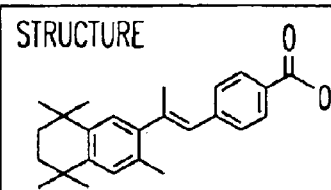
Figure 5C:
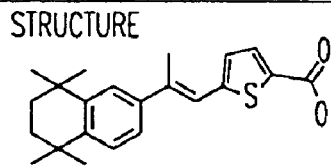
Figure 5C:
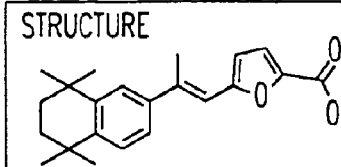
Figure 5C:
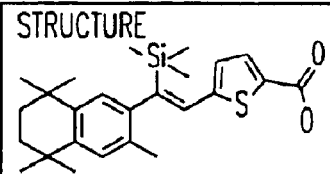
Figure 5C:
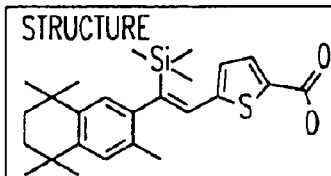
Figure 5C:
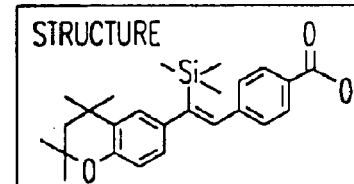
Figure 5D:
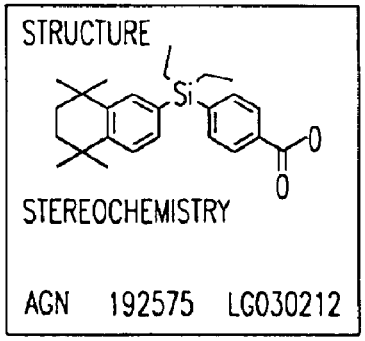
Figure 5D:
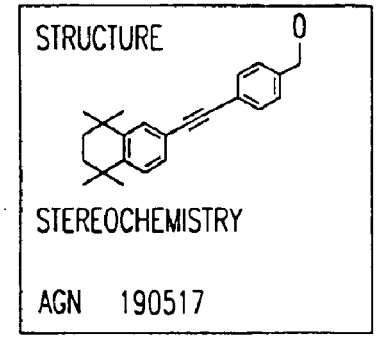
Figure 5D:
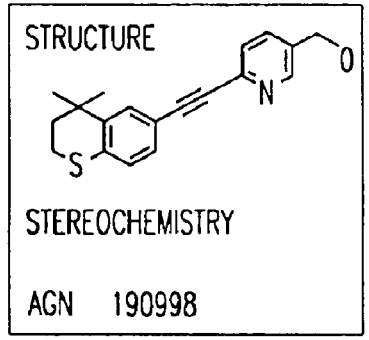
Figure 5D:
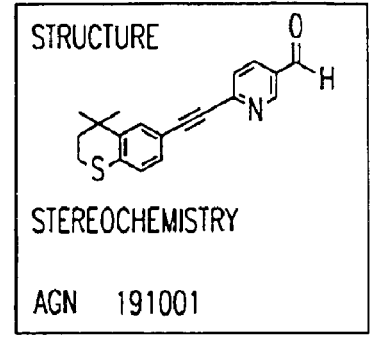
Figure 5D:
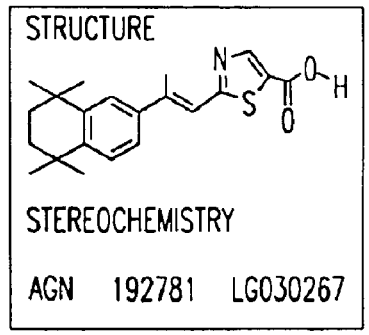

FIG. 4 shows the results of this experiment. As can be seen, the concentration-dependent ability of AGN 10 to agonize FXR transactivation activity rises in a dose-dependent fashion between concentrations of 1 and 10 $\mu$M. At this latter concentration, the FXR agonist activity of AGN 10 appears to be at a maximum in this assay system.

By contrast, as FIG. 4 shows, the activities of CDCA and DCA remain at baseline up to 10 $\mu$M, then rise in approximately linear fashion to their maxima, at about 100 $\mu$M. LCA also has a very low activity until reaching a concentration of 10 $\mu$M, but then the activity rises between 10 and 100 $\mu$M. The maximum activity of DCA and LCA is respectively about ½ and ¼ that of AGN 10, while the maximum activity of CDCA at 100 $\mu$M is roughly that of AGN 10 at 10 $\mu$M.

EXAMPLE 5

To screen additional compounds for FXR agonist activity, a panel of compounds was assembled. These compounds were: TRNPB (which has FXR activity), Am 580 (which does not have FXR activity), juvenile hormone (JH) III (50 $\mu$M) (an FXR agonist); all-trans retinoic acid (a naturally occurring RAR agonist); 9-cis retinoic acid (an RXR agonist); LG 268, LG 69 (synthetic RXR agonists); and 28 compounds designated AGN 1 through AGN 28.

The structures of AGN 1 through AGN 28 are provided in FIGS. 5a, 5b, 5c, and 5d.

The structure of Am 580 is:

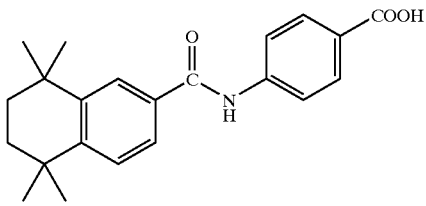

The structure of LG 69 is:

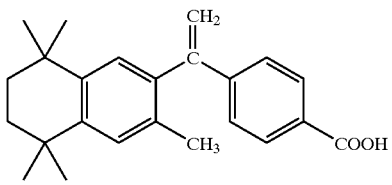

The structure of juvenile hormone III (JH III) is:

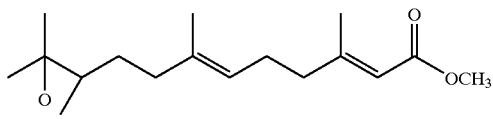

The structure of TTNPB is:

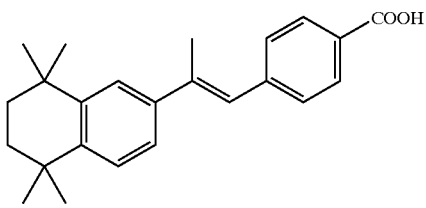

These compounds were assayed for FXR modulating activity using the transactivation assay described above. All compounds were dissolved in DMSO. As above, the reporter plasmid contained 6 copies of the ecdysone response element (EcRE) placed along with the herpes virus thymidine kinase promoter upstream of the firefly luciferase gene. The reporter plasmid was transfected into CV-1 cells, either a) alone, b) with an expression plasmid encoding full length FXR, c) with an expression plasmid encoding full length RXRα, d) with two expression plasmids encoding full length FXR and RXRα respectively, and e) with two expression plasmids encoding full length FXR and $RXR_m$, respectively. Plasmid constructions, transfection, incubation with test compounds, and luciferase activity assays were performed as described in Example 1.

Figure 6:
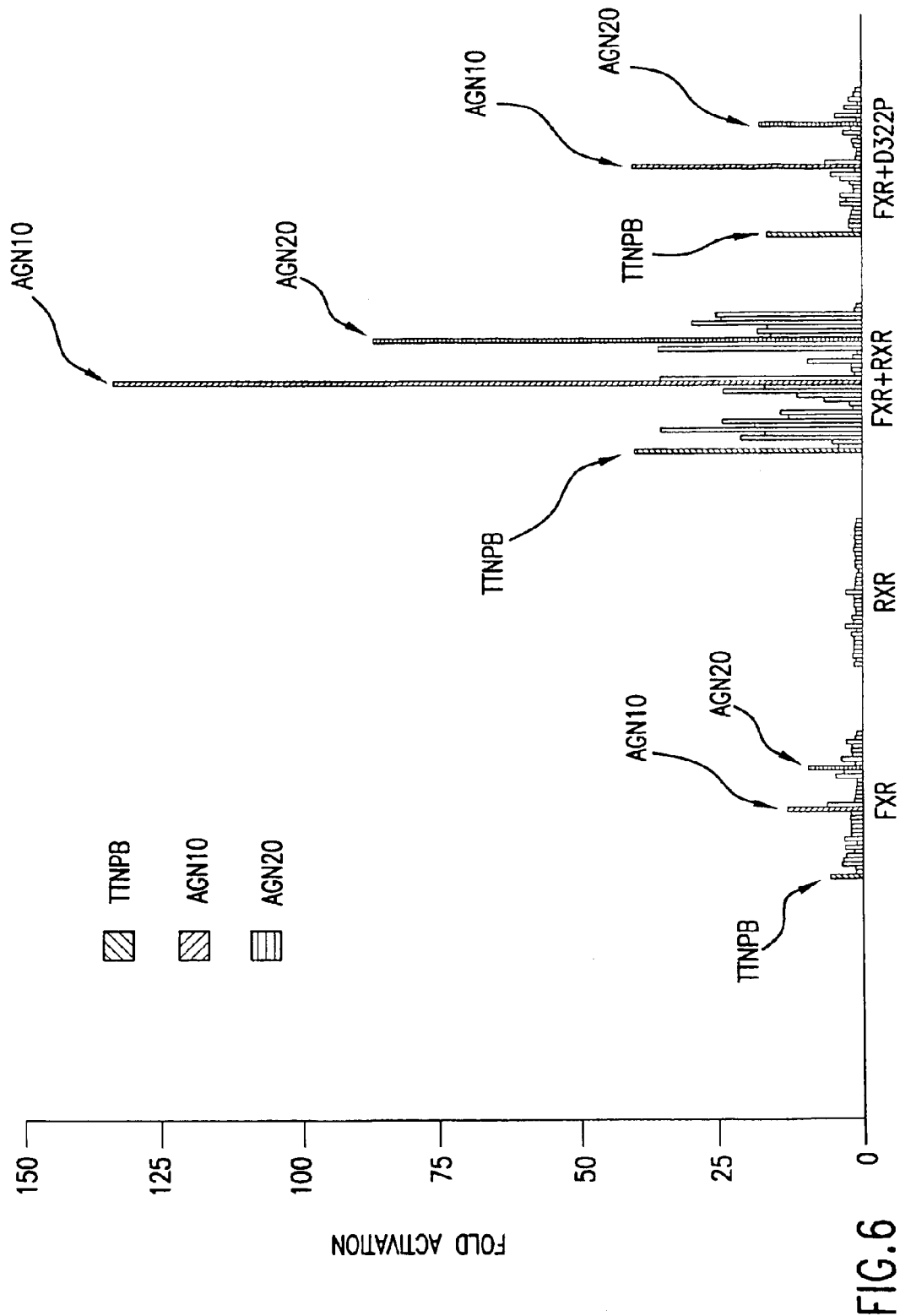
FIG. 6 provides a graph comparing the FXR agonist activities of the compounds of FIGS. 5a–5d in the presence and absence of FXR alone, RXRα alone, a FXR-RXR heterodimer and a FXR-RXRm heterodimer.

The results are shown in FIG. 6. Virtually no transactivation activity was seen in the absence of FXR and RXRα. Upon transfection of the cells with FXR alone, no significant increase in the baseline activity was seen. When cells were transfected with RXRα alone, no increase in activity over baseline could be seen. Cells cotransfected with the reporter plasmid and both FXR and RXRα expression plasmids generally responded with a considerable increase in luciferase activity upon challenge with the test compounds. Those cells given TINPB, AGN 10 and AGN 20 again gave the highest activity response. Finally, cells cotransfected with both FXR and $RXR_m$ provided a much more discriminating activity profile; the overall extent of transactivation activity was universally decreased, and only TTNPB, AGN 10 and AGN 20 showed significant levels of transctivation activity.

However, upon cotransfection with FXR and either RXRα or RXRm, significant ligand-dependent transactivation occurs. This is almost certainly due to the formation of FXR-RXR heterodimers, and shows that the ability of both FXR and RXR to promote transactivation is highly dependent upon heterodimer formation. Use of RXRm as a heterodimeric partner with FXR permits FXR-specific ligands to be distinguished from those acting on the RXR half of the heterodimer pair.

Finally, the data show that AGN 10 and AGN 20 are FXR agonists, and that ligand-dependent activation of FXR can occur without ligand-dependent priming of RXR.

The following example provides a detailed description of compounds having FXR modulating activity, as well as methods of making such compounds. Those of skill in the art will recognize that the structures of the FXR agonists AGN 10, CDCA and DCA may be used to select one or more common feature for the molecular modeling of other FXR agonists. Without limitation, some of these features include the presence of an acidic group on the right hand side of the structure, the presence of a ring or ringlike structure in the position of the trimethylsilane group of AGN 10, and perhaps the addition of one or more hydroxyl group to the psuedo naphthyl nucleus of these compounds.

Similarly, much is known about the type of modifications that may be made to an agonist to convert it into an antagonist. Thus, creation of FXR antagonists or inverse agonists, given the structure of a strong receptor agonist like AGN 10, is possible. Indeed, such modifications to a receptor agonist have already been made in the design of antagonists and inverse agonists of the retinoid receptors. See e.g., U.S. Pat. No. 5,776,699, incorporated by reference herein. Since an agonist binds to the LBD of the nuclear hormone to exert its effect, the modification of such an agonist to create a receptor antagonist generally involves retention of the same general structure as the agonist (thus permitting the antagonist to continue to bind the receptor) combined with the addition of somewhat "bulky" groups to prevent the specific conformational changes of the receptor that result in activation of the gene transcriptional functions of the receptor.

Thus, in the present case, an FXR antagonist or inverse agonist would be expected by the person or ordinary skill in the art to have a structure similar to that of AGN 10, but to contain modifications including, without limitation, addition of an aryl group to the six-membered non-aromatic ring, particularly at the uppermost position of the ring (relative to Formulae 1–5, infra); addition of an alkyl group greater than C2, or an aryl group at the silyl moiety, and addition of an aryl group to the unsubstituted carbon of the double bond to the right of the trimethylsilyl substitution of AGN 10. Other such modifications will be apparent to the person of skill in the art, and are contained in the following Example and the claims that conclude this specification.

EXAMPLE 6

Preferred FXR-Modulating Compounds, and their Synthesis

General Embodiments and Synthetic Methodology

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1, 2, 3 or 4 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

By "synthetic compound" is meant an organic compound that does normally not occur in a mammal. Specifically, a synthetic compound is meant to exclude a naturally occurring bile acid.

By "ligand" is meant a compound able to bind to a given biological molecule, or a set of isotypes of a given biological molecule, with a high degree of avidity and specificity.

By "synthetic FXR ligand" is meant a synthetic compound that is able to bind to an FXR receptor protein with a high degree of avidity and specificity.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amide has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond. Unless it is specifically stated otherwise the invention covers trans as well as cis isomers. Where the chemical name indicates a specific isomer, that designation by name is intended to control over a structure that may be ambiguously drawn or shows a different isomer.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

With reference to the symbol Y in Formulas 1, 2, 3 and 4 the preferred compounds of the invention are those where Y is phenyl, naphthyl, pyridyl, thienyl or furyl. Even more preferred are compounds where Y is phenyl. As far as substititutions on the Y (phenyl) and Y (pyridyl) groups are concerned, compounds are preferred where the phenyl group is 1,4 (para) substituted and where the pyridine ring is 2,5 substituted. (Substitution in the 2-position in the "pyridine" nomenclature corresponds to substitution in the 6-position in the "nicotinic acid" nomenclature.) In the presently preferred compounds of the invention there is no R$_2$ substituent on the Y group.

The A-B group of the preferred compounds is (CH$_2$)$_q$COOH or (CH$_2$)$_q$—COORS, where R$_8$ is defined as above. Even more preferably q is zero and R$_8$ is lower alkyl or (trialkylsilyl)ethyl(or alkyl) or (trimethylsilyl)ethyl and more preferably R$_8$ is hydrogen. Compounds are also preferred where the A-B group is CH$_2$OH.

With reference to the group X in Formulas 1 and 3, in the presently preferred compounds of the invention X is 0 (chroman or chromene compounds) or X represents C(R$_1$)$_2$ (tetrahydronaphthalene or dihydronaphthalene derivatives). Even more preferably R$_1$ of C(R$_1$)$_2$ is methyl.

R$_2$ is preferably hydrogen or lower alkyl, even more preferably methyl and R$_2$ is preferably in the 3 position of the tetrahydronaphthalene and dihydronaphthalene moiety, and preferably in the 8 position of the chroman, chromen, thiochroman, thiochromen, dihydro or tetrahydroquinoline moiety. When R$_2$ is other than hydrogen then preferably there is only one R$_2$ substituent in the aromatic portion of the condensed ring.

R$_3$ is preferably hydrogen or methyl. Presently most preferred substitution of the non-aromatic portion of the condensed ring when the dashed line represents absence of a bond in Formulas 1 and 3 is such that there are geminal dimethyl groups in the 2 or 4 positions, or in both when X is a heteroatom, and geminal dimethyl groups in the 5 and 8 positions when the condensed ring is tetrahydronaphthylene and geminal dimethyl groups in the 5-position when the condensed ring is dihydronaphthalene. When the dashed line represents a bond, R$_3$ is preferably (R$_{15}$)$_r$-phenyl, (R$_{15}$)$_r$-naphthyl, or (R$_{15}$)$_r$-heteroaryl, more preferably (R$_{15}$)$_r$- phenyl, or $(R_{15})_r$-thienyl and $R_{15}$ preferably is an alkyl group. As represented herein, numbering of the bicyclic ring structure is as follows.

In the presently preferred compounds of the invention the silicon containing substituent is preferably attached at the 6 position of the chroman, chromene, thiochroman, thiochromene, tetrahydroquinoline or dihydroquinoline nucleus, and to the 2 position of the tetrahydronaphthalene or dihydronaphthalene nucleus.

The present specific examples of the compounds of the invention are disclosed in TABLE 1 with reference to Formula 5 and Formula 6 and their preparation by the presently preferred synthetic methodology is described in the experimental section of this application.

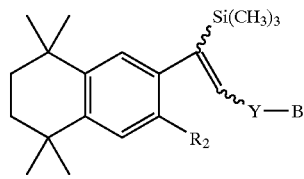

Formula 5

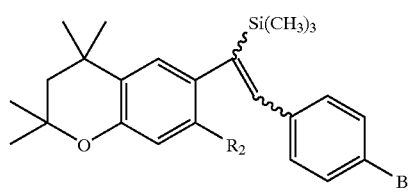

Formula 6

TABLE 1

| Compound | Formula | $R_2$ | Y | B |
|---|---|---|---|---|
| 3 | 5 | $CH_3$ | 1,4 substituted phenyl | $CH_2OH$ |
| 4 | 5 | $CH_3$ | 1,4 substituted phenyl | COOEt |
| 5 | 5 | $CH_3$ | 1,4 substituted phenyl | COOH |

TABLE 1-continued

| Compound | Formula | $R_2$ | Y | B |
|---|---|---|---|---|
| 6 | 5 | H | 1,4 substituted phenyl | $CH_2OH$ |
| 7 | 5 | H | 1,4 substituted phenyl | COOEt |
| 8 | 5 | H | 1,4 substituted phenyl | COOH |
| 10 | 6 | H | — | COOEt |
| 11 | 6 | H | — | COOH |
| 14 | 5 | $CH_3$ | 2,5 substituted thienyl | $CH_2OH$ |
| 15 | 5 | $CH_3$ | 2,5 substituted thienyl | COOEt |
| 16 | 5 | $CH_3$ | 2,5 substituted thienyl | COOH |
| 17 | 5 | H | 2,5 substituted thienyl | $CH_2OH$ |
| 18 | 5 | H | 2,5 substituted thienyl | COOEt |
| 19 | 5 | H | 2,5 substituted thienyl | COOH |

The compounds of the invention can be made by the generalized synthetic route shown in Reaction Scheme 1, 1a and Reaction Scheme 2.

Referring now to Reaction Scheme 1 and Reaction Scheme 1a, a presently preferred synthetic route to compounds of the invention of Formula 3 is disclosed. In accordance with Scheme 1 a bromoarylmethyl alcohol compound of Formula 7 is the starting material. In Formula 7 the symbols Y and $R_2$ are defined as in connection with Formulas 1–4. Examples for the compounds of Formula 7 which are used for the synthesis of presently preferred exemplary compounds of the invention are 4-bromobenzyl alcohol and (5-bromothiophen-2-yl)-methyl alcohol. Other examples are 3-bromobenzyl alcohol, (6-bromopyridin-3-yl)methyl alcohol and (5-bromofuran-2-yl)methyl alcohol. These starting materials are either available commercially or can be readily obtained in accordance with the chemical literature. The alcohols of Formula 7 are reacted with a reagent that introduces a protecting group on the primary alcohol function. An example of a suitable reagent to introduce the protecting group and one that is used in the synthesis of the presently preferred compounds of the invention is tert-butyldiphenylsilyl chloride shown in Reaction Scheme 1. The product of the reaction with tert-butyldiphenylsilyl chloride (conducted in the presence of base) is a (bromoaryl)methyl t-butyldiphenylsilyl ether of Formula 8.

REACTION SCHEME 1

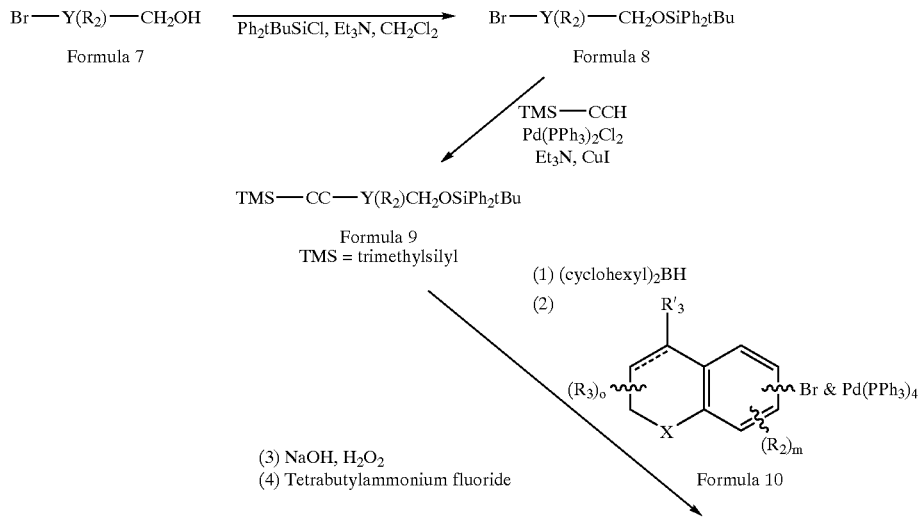

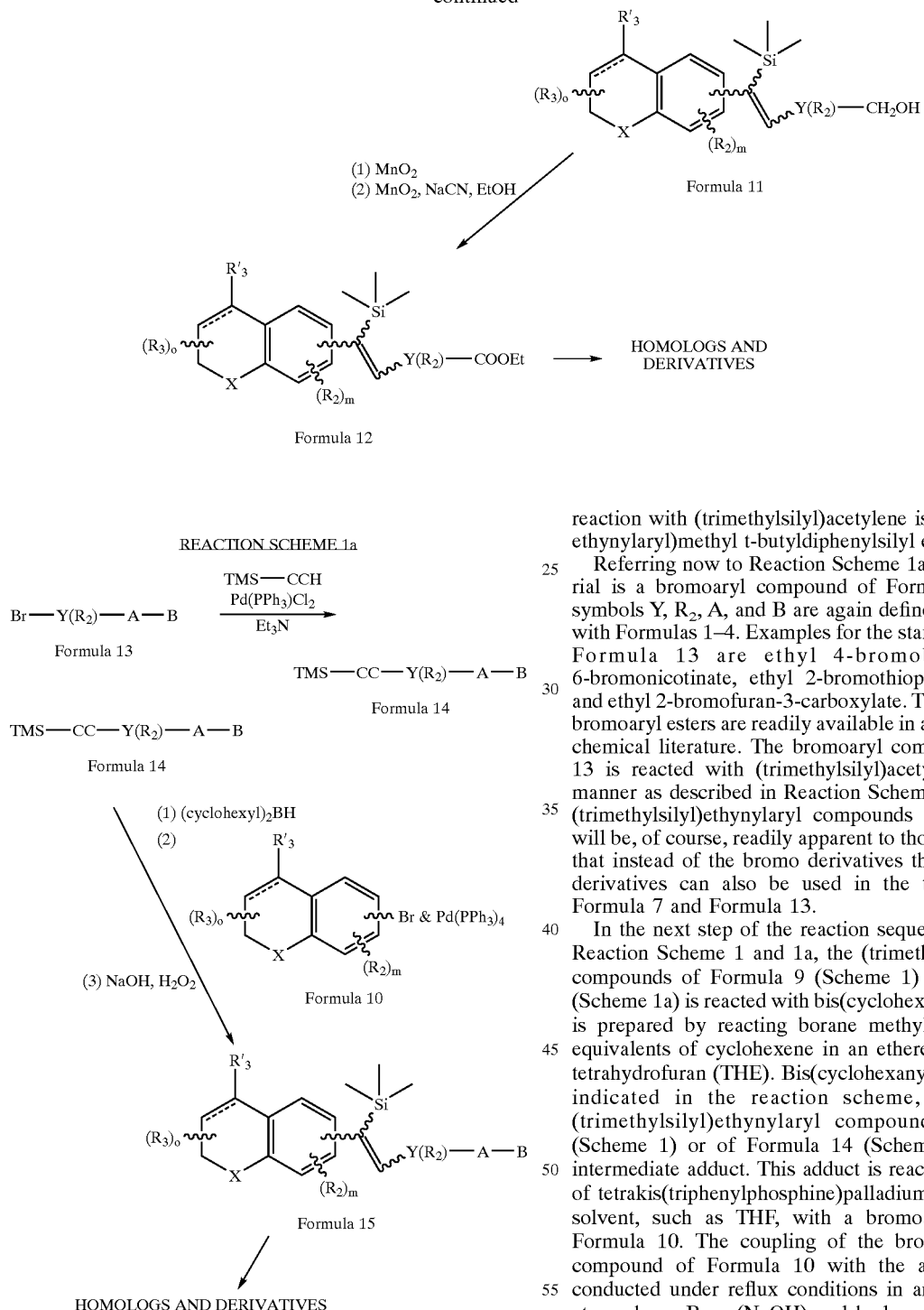

REACTION SCHEME 1a

Formula 13 / Formula 14 / Formula 10 / Formula 15

HOMOLOGS AND DERIVATIVES

The (bromoaryl)methyl t-butyldiphenylsilyl ether of Formula 8 is reacted with (trimethylsilyl)acetylene in the presence of bis(triphenylphosphine)palladium (II) chloride catalyst, copper (I) iodide and a suitable base such as triethyl amine. The latter coupling reaction of a bromoaryl compound with (trimethylsilyl)acetylene in the presence of a palladium complex catalyst per se is well known in the art, and is described for example in U.S. Pat. Nos. 5,663,347 and 5,808,083 the specification of which are expressly incorporated herein by reference. The product of the coupling reaction with (trimethylsilyl)acetylene is a ((trimethylsilyl)ethynylaryl)methyl t-butyldiphenylsilyl ether of Formula 9.

Referring now to Reaction Scheme 1a, the starting material is a bromoaryl compound of Formula 13 where the symbols Y, $R_2$, A, and B are again defined as in connection with Formulas 1–4. Examples for the starting compounds of Formula 13 are ethyl 4-bromobenzoate, ethyl 6-bromonicotinate, ethyl 2-bromothiophene-3-carboxylate and ethyl 2-bromofuran-3-carboxylate. These and analogous bromoaryl esters are readily available in accordance with the chemical literature. The bromoaryl compound of Formula 13 is reacted with (trimethylsilyl)acetylene in the same manner as described in Reaction Scheme 1, to provide the (trimethylsilyl)ethynylaryl compounds of Formula 14. It will be, of course, readily apparent to those skilled in the art that instead of the bromo derivatives the appropriate iodo derivatives can also be used in the the compounds of Formula 7 and Formula 13.

In the next step of the reaction sequence shown both in Reaction Scheme 1 and 1a, the (trimethylsilyl)ethynylaryl compounds of Formula 9 (Scheme 1) or of Formula 14 (Scheme 1a) is reacted with bis(cyclohexanyl)borane, which is prepared by reacting borane methyl sulfide with two equivalents of cyclohexene in an ethereal solvent such as tetrahydrofuran (THE). Bis(cyclohexanyl) borane, which is indicated in the reaction scheme, reacts with the (trimethylsilyl)ethynylaryl compounds of Formula 9 (Scheme 1) or of Formula 14 (Scheme 1a) to form an intermediate adduct. This adduct is reacted in the presence of tetrakis(triphenylphosphine)palladium (0) in an ethereal solvent, such as THF, with a bromoaryl compound of Formula 10. The coupling of the bromo (or iodo) aryl compound of Formula 10 with the adduct is typically conducted under reflux conditions in an inert (argon) gas atmosphere. Base (NaOH) and hydrogen peroxide is then added to the reaction mixture to provide the (trimethylsilyl)vinyl product of Formula 15 in Scheme 1a. In accordance with Scheme 1 product of the coupling reaction still includes the diphenyl-t-butylsilyl protecting group which is removed by treatment with tetrabutylammonium fluoride to give the (trimethylsilyl)vinyl)aryl methyl alcohol derivatives of Formula 11.

The condensed cyclic bromoaryl compounds of Formula 10 which are used in the coupling reaction are available in accordance with the chemical scientific or patent literature, or can be obtained within the skill of the ordinary artisan in analogy to synthetic processes known in the scientific or patent literature. Examples for compounds of Formula 10 which are used for the preparation of presently preferred compounds of the invention are 2-bromo-3,5,5,8,8-pentamethyl-5,6,7,8-tetrahydronaphthalene, 2-bromo-5,5,8, 8-tetramethyl-5,6,7,8-tetrahydronaphthalene and 6-bromo-2,2,4,4-tetramethylchroman. Further examples are 6- or 7-bromo-4,4-dimethylchroman, 6- or 7-bromo-4,4-dimethylthiochroman and 2 or 3 bromo tetrahydroquinoline derivatives which are available in accordance with the teachings of U.S. Pat. Nos. 5,348,972, 5,053,523 and 5,877,207 the specifications of which are incorporated hereby reference. As still further examples U.S. Pat. Nos. 5,278,318, and 5,407,937, describe 2-alkyl and/or 4-alkyl substituted thiochromans also substituted with a bromo group in the 6 position. U.S. Pat. No. 5,346,895 describes 2-alkyl and/or 4-alkyl substituted thiochromans substituted with a bromo group in the 7 position. U.S. Pat. Nos. 5,324,744, 5,348,975 and 5,346,895 describe 2-alkyl and/or 4-alkyl substituted chromans substituted with a bromo group in the 7 position. U.S. Pat. No. 5,348,972 describes 4-alkyl substituted tetrahydroquinoline compounds substituted with a bromo group in the 2-position. The specifications of U.S. Pat. Nos. 5,278,318, 5,324,744, 5,346,585, 5,348,975, and 5,407,937 are also expressly incorporated herein by reference.

Condensed cyclic bromoaryl compounds of Formula 10 where the dashed line represents a bond, and particularly those where the dashed line represents a bond and the $R'_{13}$ substituent is an aryl or heteroaryl group, can be obtained from the corresponding brominated chroman-4-one, thiochroman-4-one, tetrahydroquinoline-4-one, and tetrahydronaphthalenone derivatives by first forming the (trifluoromethyl)sulfonyloxy derivatives from the oxo functionality, and thereafter reacting those with an (organometallic) derivative that introduces the $R'_3$ group in analogy to the reactions described in U.S. Pat. No. 5,877,207. Alternatively, the compounds of the invention where the dashed line represents a bond and the $R^1_3$ substituent is an aryl or heteroaryl group, can be obtained from the corresponding (trimethylsilyl)vinyl derivatives that include an oxo function in the 4-position of the chroman, thiochroman or tetrahydroquinoline, and in the 8-position of tetrahydronaphthalene nucleus. These reactions are also conducted through the (trifluoromethyl)sulfonyloxy intermediates, in analogy to the teachings of U.S. Pat. No. 5,877,207.

Referring now again to Reaction Scheme 1, the primary alcohol derivatives of Formula 11 are compounds within the scope of the invention, particularly within the scope of Formula 3. The primary alcohols can be oxidized to the ester stage, for example as shown in Scheme 1, by treatment with manganese dioxide that first oxidizes the primary alcohol to the aldehyde stage, and thereafter by treatment of the aldehyde with manganese dioxide and sodium cyanide in alcohol, to provide the ethyl ester derivatives of Formula 12. The compounds of Formula 11, and 12 in Reaction Scheme 1, and the compounds of Formula 15 in Reaction Scheme 1a can be converted to further compounds of the invention by synthetic procedures which are well known in the art. This is indicated in Reaction Schemes 1 and 1a as conversion to "Homologs and Derivatives" and the transformations symbolized here primarily refer to reactions of the group designated A-B in the formulas. In these and related reactions the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOrnie, Plenum Publishing Press, 1973 and Protecting Groups, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 14 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/ oxalyl chloride in methylene chloride (Omura, K., Swern, D., Tetrahedron. 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

The compounds of the invention which are in accordance with Formula 4 can be prepared in analogy to the synthetic routes described in Reaction Schemes 1 and 1a. In order to obtain these compounds of the invention, a halogenated benzene derivative, such as bromobenzene, iodobenzene (or a subtituted derivative thereof where the substituent is $R_2$) is reacted with the (trimethylsilyl)ethynylaryl compounds of Formula 9 (Scheme 1) or of Formula 14 (Scheme 1a).

Referring now to Reaction Scheme 2, a synthetic route is described to obtain compounds of the invention in accordance with Formula 1.

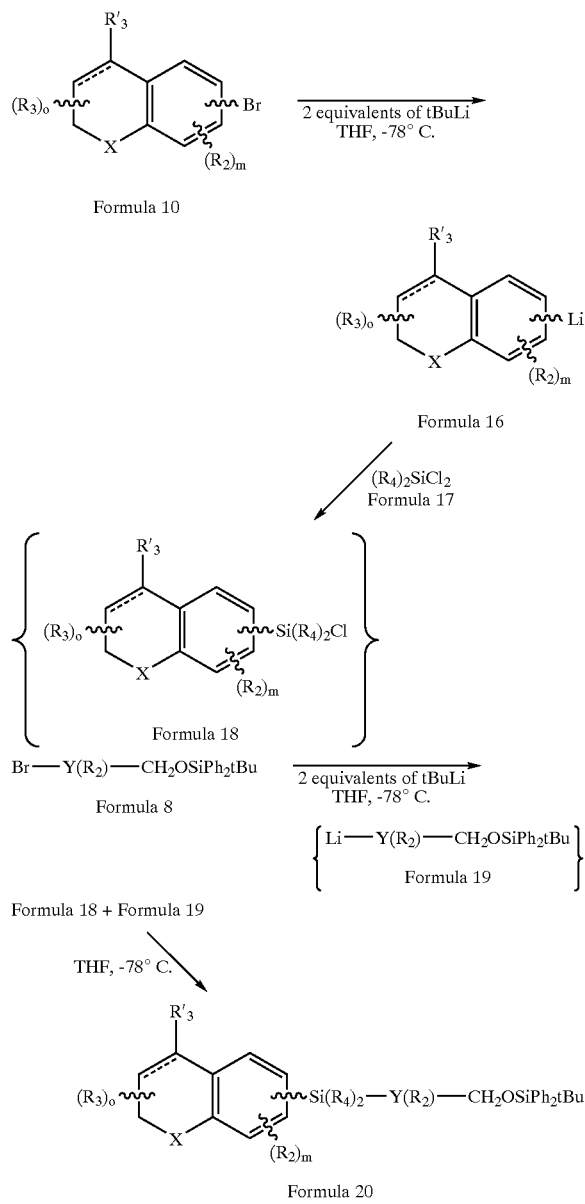

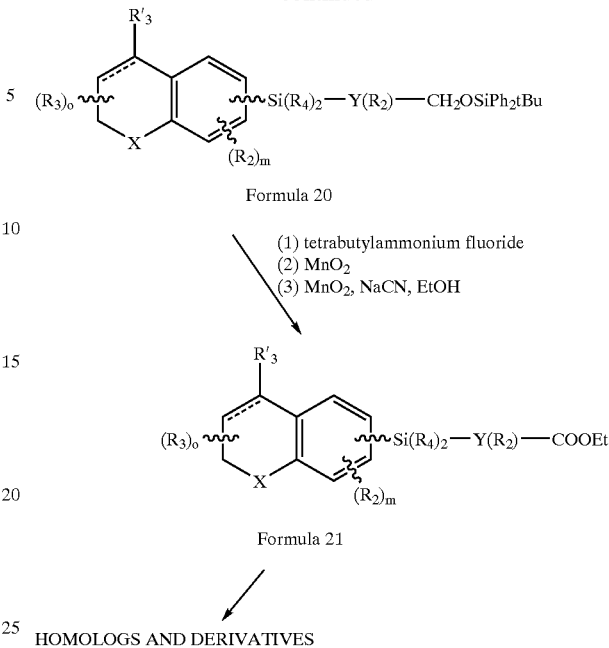

HOMOLOGS AND DERIVATIVES

The starting compounds utilized in Reaction Scheme 2 are the condensed cyclic bromoaryl compounds of Formula 10, which have been described above in connection with Reaction Scheme 1, and 1a. The bromo aryl compounds of Formula 10 are converted into an organometallic, preferably, organolithium reagent, as is shown in Scheme 2. Exchange of the bromine (or of iodine if an iodoaryl reagent is used) with lithium is conducted under conditions normally practiced in the art, typically with two equivalents of tert-butyl lithium, in an ethereal reagent (THF) in the cold, typically −78° F. The resulting condensed cyclic aryl lithium reagent of Formula 16 is then reacted with a dialkyldichlorosilane, alkylphenyldichlorosilane or diphenyldichlorosilane reagent of Formula 17. The $R_4$ groups in Formula 17 have the same definition as in connection with Formulas 1–4. The dialkyldichlorosilane, alkylphenyldichlorosilane or diphenyldichlorosilane reagents are available commercially, or can be prepared in accordance with known procedures within the skill of the ordinary practitioner in the field.

As is shown in Reaction Scheme 2, with the bromoaryl compound of Formula 10 the $(R_4)_2SiCl_2$ reagent forms an aryl dialkylchlorosilane of Formula 18. The latter is typically not isolated, but used without isolation to react with an organolithium compound of Formula 19 that is also prepared by bromine-lithium exchange from the (bromoaryl)methyl t-butyldiphenylsilyl ether of Formula 8, described above in connection with Reaction Scheme 1. The (aryl)methyl t-butyldiphenylsilyl ether lithium reagent of Formula 19 is also typically not isolated before reacting it with the reagent of Formula 18. This is indicated in the reaction scheme by placing the reagents of Formulas 18 and 19 in large square brackets.

The product of the reaction between the aryl dialkylchlorosilane of Formula 18 and the (aryl)methyl t-butyldiphenylsilyl ether lithium reagent of Formula 19 is the diarylsilane compound of Formula 20 that still has the tert-butyldiphenylsilyl protecting group on the primary alcohol function. This is removed by treatment with tetrabutylammonium fluoride, and the resulting primary alcohol can be oxidized to the ester stage (Formula 21) in analogy to the reactions described in connection with Reaction Scheme 1. The diarylsilane compounds of Formula 21 are within the scope of the invention, particularly within the scope of Formula 1 and can be converted into further homologs and derivatives, as described above. A particularly preferred step of such conversion is saponifaction of the ester group with base to provide the free carboxylic acids (or salts thereof) of the invention.

The diarylsilane compounds of Formula 2 can be prepared in analogy to the preparation of the diarylsilane compounds of Formula 1. A starting material in this synthetic route is a halogenated benzene derivative, such as bromobenzene, iodobenzene or a substituted derivative thereof where the substituent is $R_2$.

REACTION SCHEME 3

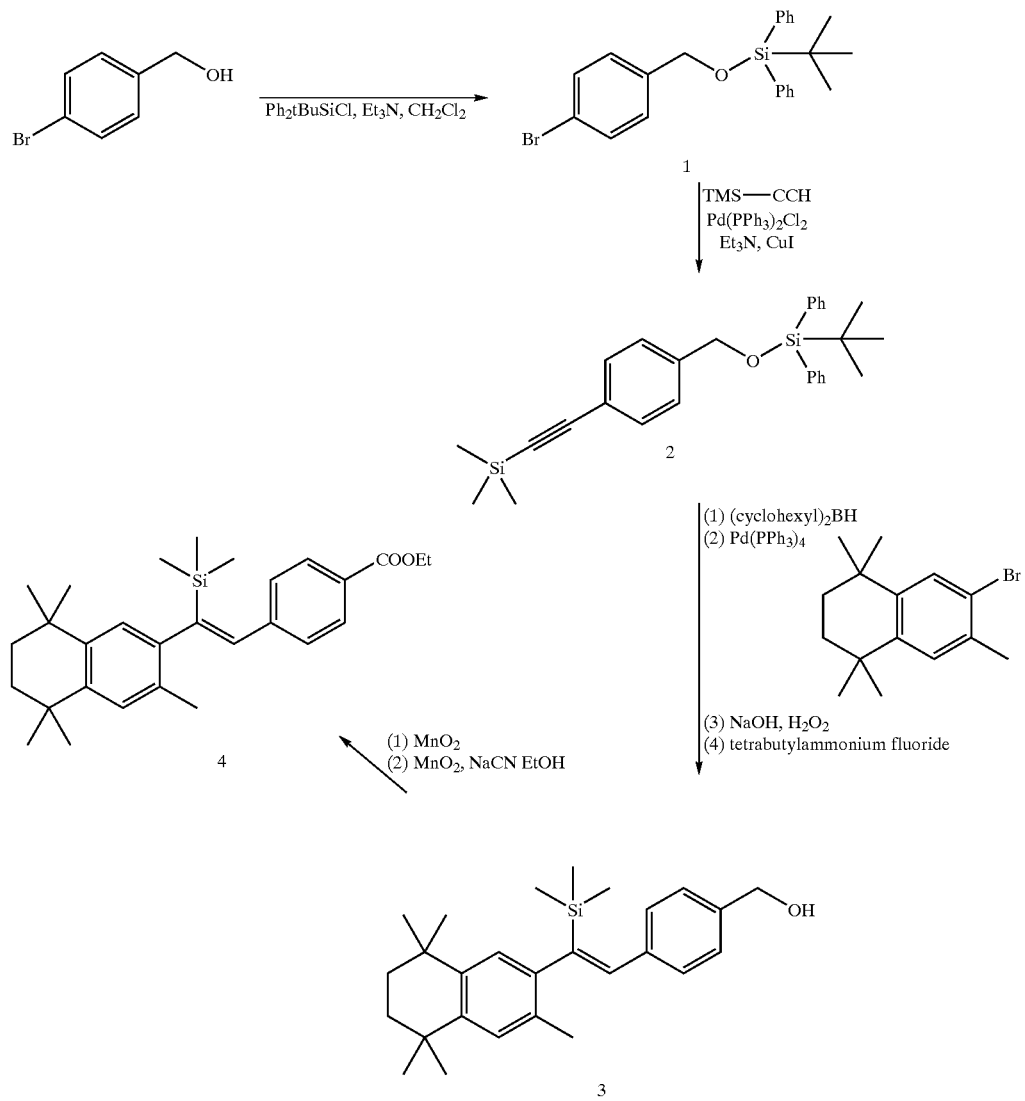

REACTION SCHEME 4

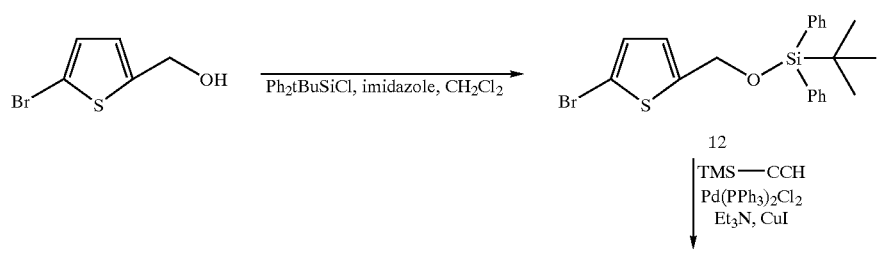

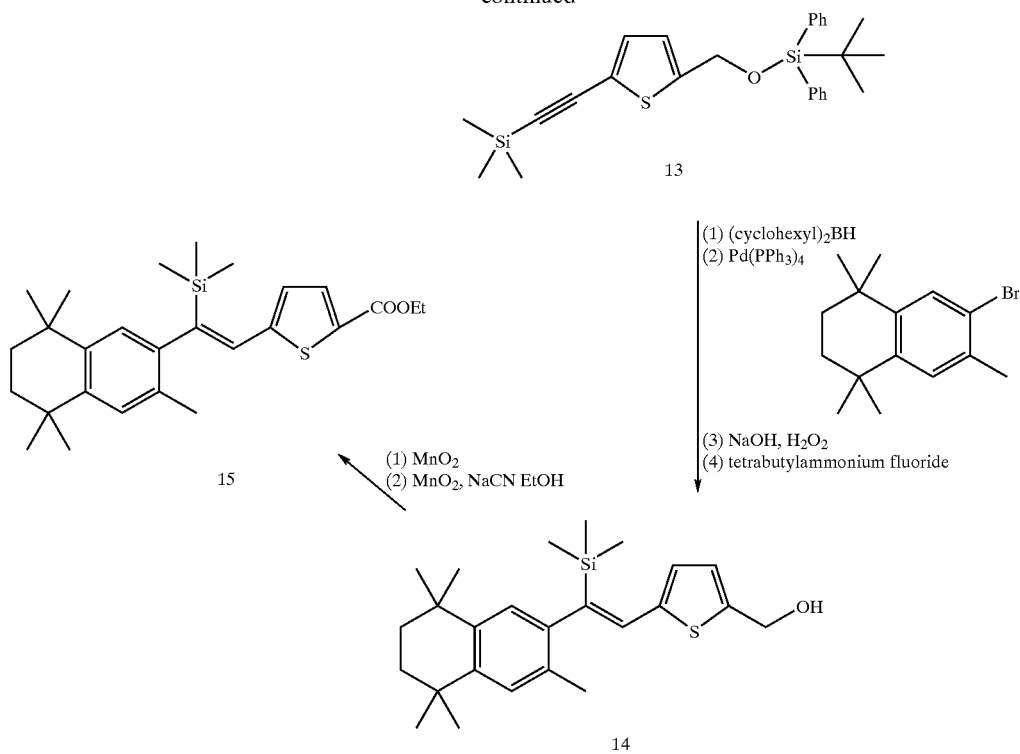

Reaction Schemes 3 and 4 illustrate the synthesis of certain exemplary compounds of the invention. The synthetic processes illustrated in these two schemes are described in detail in the section titled "Specific Chemical Examples" below.

SPECIFIC CHEMICAL EXAMPLES

4-Bromobenzyl tert-butyldiphenylsilyl ether (Compound 1)

Tert-butyldiphenylsilyl chloride (10.4 mL, 40.1 mmol) was added to a solution of 4-bromobenzyl alcohol (5.0 g, 26.7 mmol) and 50 mL of dichloromethane. The solution was treated with triethylamine (3.72 mL, 26.7 mmol) and (dimethylamino)pyridine (163 mg, 1.34 mmol) and stirred overnight at room temperature. The solution was diluted with 300 mL of dichloromethane and washed with 50 mL of 10% aqueous HCl. The layers were separated and the aqueous layer was extracted with 50 mL of dichloromethane. The combined organic extracts were washed with brine, and dried (MgSO$_4$), and filtered, and the solvents were removed in vacuo. The residue was filtered through a plug (6@×2@) of silica gel using a solution of 97% hexane/ethyl acetate. After removal of the solvent the residue was heated under vacuum (3 torr) to 170° C. for 1 hour to remove a low-boiling impurity. The remaining material is the title compound.

PNMR (300 MHz, CDCl$_3$)• 1.09 (s, 9H), 4.70 (s, 2H), 7.20 (d, 2H, J=7.9 Hz), 7.35–7.45 (m, 8H), 7.65 (overlapping ds, 4H).

4-[(trimethylsilyl)ethynyl]benzyl tert-butyldiphenylsilyl ether (Compound 2)

A 25 mL round bottom flask was flame-dried under high vacuum. The vacuum was broken by the addition of dry argon, and the flask was allowed to cool to room temperature. The flask was charged with 2.0 g (4.70 mmol) of 4-bromobenzyl tert-butyldiphenylsilyl ether (Compound 1), 2.0 mL (14.1 mmol) of (trimethylsilyl)acetylene, and 16.5 mL of triethylamine. The solution was purged with argon for 15 minutes and bis(triphenylphosphine)palladium (II) chloride (83 mg, 0.12 mmol) and copper (I) iodide (22 mg, 0.12 mmol) were added and the solution stirred at ambient temperature for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by distillation (bp=180° B 185° C., 1 torr) to give the title compound.

PNMR (300 MHz, CDCl$_3$)• 0.23 (s, 9H), 1.09 (s, 9H), 4.73 (s, 2H), 7.23 (d, 2 H, J=7.9 Hz), 7.31–7.45 (m, 8H), 7.65 (overlapping ds, 4H).

(Z)-4-[2-(3,5,5,8,8-Pentamethyl-5,6,7,8-tetrahydronaphthalen-2-yl)-2-(trimethylsilyl)vinyl]benzyl alcohol (Compound 3) General Procedure A A 3-neck 25 mL round bottom flask was fitted with a reflux condenser, and flame-dried under high vacuum. The vacuum was broken by the addition of dry argon (3×), and the flask was allowed to cool to room temperature. The flask was charged with 0.5 mL (1.0 mmol) of borane-methyl sulfide and THF (0.3 mL) and cooled to 0° C. The solution was treated with 0.20 mL (2 mmol) of cyclohexene and stirred at 0° C. for 1 hour. Neat 4-[(trimethylsilyl)ethynyl]benzyl tert-butyldiphenylsilyl ether (Compound 2, 443 mg, 1 mmol) was added and, after 15 minutes the solution was warmed to room temperature and stirred for 2.25 hours. In a second flask was prepared a solution of tetrakis(triphenylphosphine)palladium (0) (58 mg, 0.05 mmol) and 2-bromo-3,5,5,8,8-pentamethyl-5,6,7, 8-tetrahydronaphthalene (1.26 g, 4.5 mmol) in 5 mL of THF, which was purged with argon for 10 minutes. The solvents in the first flask were removed under high vacuum, and the residue dissolved in 1 mL of THF and 1 mL of 2 M aqueous NaOH, and the resulting solution was purged with argon for 10 minutes. A 1 mL aliquot of the solution from the second flask was added to the first flask, and the reaction was protected from light and refluxed for 5 hours. The reaction was cooled to room temperature and treated with 2 M NaOH (1 mL) and 30% hydrogen peroxide (0.4 mL). The solution was poured into a separatory funnel containing water and pentane. The layers were separated and the aqueous layer was extracted 3 times with pentane. The combined organic layers were washed once with brine, and dried over magnesium sulfate, and the solvents were removed under reduced pressure. The residue was partially purified by silica gel chromatograhy (99:1, hexane:ethyl acetate). The later fractions were combined and concentrated under reduced pressure. The residue (203 mg) was dissolved in 3.2 mL of THF and treated with 313 mg of tetrabutylammonium flouride (Tbaf) adsorbed onto silica gel (1.6 mmol flouride per gram). The suspension was stirred for 5 hours at room temperature and then the silica gel was washed with ether, and the separated ether extracts were dried over magnesium sulfate. The filtered solvents were removed under reduced pressure and the residue purified by silica gel chromatography (4:1, hexane:ethyl acetate) to give the title compound.

PNMR (300 MHz, $CDCl_3$)-0.10 (s, 9H), 1.29 (s, 12H), 1.68 (s, 4H), 2.24 (s, 3H), 4.72 (s, 2H), 6.87 (s, 1H), 7.07 (s, 1H), 7.17 (s, 1H), 7.35 (s, 4H).

Ethyl(Z)-4-[2-(3,5,5,8,8-pentamethyl-5,6,7,8-tetrahydronaphthalen-2-yl)-2-(trimethylsilyl)vinyl] benzoate (Compound 4) General Procedure B Manganese dioxide (265 mg, 2.96 mmol) was added to a solution of (Z)-4-[2-(3,5,5,8,8-pentamethyl-5,6,7,8-tetrahydronaphthalen-2-yl)-2-(trimethylsilyl)vinyl]benzyl alcohol (Compound 3, 60 mg, 0.15 mmol) and 3.65 mL of hexane. The solution was stirred at room temperature for 16 hours, the manganese dioxide filtered off, and the hexane removed in vacuo. The residue was dissolved in 2 mL of ethanol and treated with sodium cyanide (37.5 mg, 0.77 mmol) and acetic acid (13.7 mg, 0.23 mmol). After 15 minutes, the solution was treated with 265 mg (3.0 mmol) of manganese dioxide. The suspension was stirred at room temperature for 6 hours and the manganese dioxide removed by filtration. The solution was poured into a separatory funnel containing water and ether. The layers were separated and the aqueous layer was extracted 3 times with ether. The combined organic layers were washed once with brine, and dried over magnesium sulfate, and the solvents were removed under reduced pressure. The residue was purified by silica gel chromatograhy (97:3, hexane:ethyl acetate) to give the title compound. PNMR (300 MHz, $CDCl_3$)-0.11 (s, 9H), 1.28 (s, 12H), 1.41 (t, 3H, J=7.1 Hz), 1.68 (s, 4H), 2.23 (s, 3H), 4.39 (q, 2H, J=7.1 Hz), 6.86 (s, 1H), 7.08 (s, 1H), 7.17 (s, 1H), 7.41 (d, 2H, J=8.5 Hz), 8.03 (d, 2H, J=8.5 Hz).

(Z)-4-[2-(3,5,5,8,8-Pentamethyl-5,6,7,8-tetrahydronaphthalen-2-yl)-2-(trimethylsilyl)vinyl] benzoic Acid (Compound 5) General Procedure C To a solution of ethyl(Z)-4-[2-(3,5,5,8,8-pentamethyl-5,6,7,8-tetrahydronaphthalen-2-yl)-2-(trimethylsilyl)vinyl] benzoate (Compound 4, 0.034 g, 0.076 mmol) and 2 mL of ethyl alcohol was added aqueous 1 N KOH (0.5 mL). The resulting solution was heated in an 50° C. bath until the hydrolysis reaction was completed, as judged by thin layer chromatography. The solution was cooled to room temperature, diluted with water and washed once with 1:1 ether:hexane solution, and the layers were separated. The aqueous layer was acidified with 1 N aqueous HCl and the product extracted 3 times with ethyl acetate. The combined organic extracts were washed with brine, and dried over $MgSO_4$, and filtered, and the solvents were removed in vacuo to give the title compound as a white solid.

PNMR (300 MHz, $CDCl_3$)• -0.09 (s, 9H), 1.28 (s, 12H), 1.68 (s, 4H), 2.24 (s, 3H), 6.86 (s, 1H), 7.08 (s, 1H), 7.18 (s, 1H), 7.46 (d, 2H, J=8.1 Hz), 8.11 (d, 2H, J=8.1 Hz).

(Z)-4-[2-(5,5,8,8-Tetramethyl-5,6,7,8-tetrahydronaphthalen-2-yl)-2-(trimethylsilyl)vinyl] benzyl alcohol (Compound 6)

Following General Procedure A, 4-[(trimethylsilyl) ethynyl]benzyl tert-butyldiphenylsilyl ether (Compound 2, 0.89 g, 2.0 mmol) and 2-bromo-5,5,8,8-tetramethyl-5,6,7,8-tetrahydronaphthalene (0.60 g, 2.25 mmol) were coupled to give the title compound. 2-bromo-5,5,8,8-tetramethyl-5,6,7, 8-tetrahydronaphthalene can be prepared in accordance with the procedure set forth in J. Med. Chem. 37:293041 (1994). The pentamethyl derivative thereof can be prepared in accordance with the same procedure.

PNMR (300 MHz, $CDCl_3$)-0.05 (s, 9H), 1.30 (s, 6H), 1.32 (s, 6H), 1.70 (s, 4 H), 4.72 (s, 2H), 6.97 (dd, 1H, J=2.0, 8.1 Hz), 7.10 (d, 1H, J=2.0 Hz), 7.24 (d, 1H, J=8.1 Hz), 7.28 (s, 1H), 7.33 (s, 4H).

Ethyl(Z)-4-[2-(5,5,8,8-tetramethyl-5,6,7,8-tetrahydronaphthalen-2-yl)-2-(trimethylsilyl)vinyl] benzoate (Compound 7)

Following General Procedure B, (Z)-4-[2-(5,5,8,8-tetramethyl-5,6,7,8-tetrahydronaphthalen-2-yl)-2-(trimethylsilyl)vinyl]benzyl alcohol (Compound 6, 0.50 g, 1.3 mmol) was oxidized to give the title compound.

PNMR (300 MHz, $CDCl_3$)• -0.05 (s, 9H), 1.29 (s, 6H), 1.31 (s, 6H), 1.41 (t, 3H, J=7.1 Hz), 1.69 (s, 4H), 4.39 (d, 2H, J=7.1 Hz), 6.95 (dd, 1H, J=2.0, 8.1 Hz), 7.09 (d, 1H, J=2.0 Hz), 7.24 (d, 1H, J=8.1 Hz), 7.27 (s, 1H), 7.38 (d, 2H, J=8.3 Hz), 8.02 (d, 2H, J=8.3 Hz).

(Z)-4-[2-(5,5,8,8-Tetramethyl-5,6,7,8-tetrahydronaphthalen-2-yl)-2-(trimethylsilyl)vinyl] benzoic acid (Compound 8)

Following General Procedure C, ethyl(Z)-4-[2-(5,5,8,8-tetramethyl-5,6,7,8-tetrahydronaphthalen-2-yl)-2-(trimethylsilyl)vinyl]benzoate (Compound 7, 0.205 g, 0.47 mmol) was hydrolyzed to give the title compound.

PNMR (300 MHz, $CDCl_3$)-0.04 (s, 9H), 1.29 (s, 6H), 1.32 (s, 6H), 1.70 (s, 4H), 6.97 (dd, 1H, J=2.0, 8.1 Hz), 7.09 (d, 1H, J=2.0 Hz), 7.25 (d, 1H, J=8.1 Hz), 7.29 (s, 1H), 7.43 (d, 2H, J=8.1 Hz), 8.09 (d, 2H, J=8.1 Hz).

Ethyl 4-[(trimethylsilyl)ethynyl]benzoate (Compound 9)

A resealable tube was flame-dried under high vacuum. The vacuum was broken by the addition of dry argon, and the flask was allowed to cool to room temperature. The flask was charged with 5.0 g (18.1 mmol) of ethyl 4-bromobenzoate, 7.7 mL (54.3 mmol) of (trimethylsilyl) acetylene, and 65 mL of diethylamine. The solution was purged with argon for 15 minutes and bis (triphenylphosphine)palladium (II) chloride (320 mg, 0.45 mmol) and copper (I) iodide (87 mg, 0.45 mmol) were added, the tube sealed, and the solution stirred at 55° C. for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by silica gel chromatography (95:5. hexane:ethyl acetate) to give the title compound.

PNMR (300 MHz, CDCl$_3$)• 0.26 (s, 9H), 1.39 (t, 3H, J=7.1 Hz), 4.36 (q, 2H, J=7.1 Hz), 7.51 (d, 2H, J=8.6 Hz), 7.97 (d, 2H, J=8.6 Hz).

Ethyl(Z)-4-[2-(2,2,4,4-tetramethylchroman-6-yl)-2-(trimethylsilyl)vinyl]benzoate (Compound 10)

Following General Procedure A, ethyl 4-[(trimethylsilyl)ethynyl]benzoate (Compound 9, 0.51 g, 2.0 mmol) and 6-bromo-2,2,4,4-tetramethylchroman (0.57 g, 2.25 mmol) were coupled to give the title compound.

PNMR (300 MHz, CDCl$_3$)• −0.06 (s, 9H), 1.36 (s, 6H), 1.37 (s, 6H), 1.39 (t, 3H, J=7.1 Hz), 1.85 (s, 2H), 4.38 (q, 2H, J=7.1 Hz), 6.75 (d, 1H, J=8.3 Hz), 6.94 (dd, 1H, J=2.3, 8.3 Hz), 7.07 (s, 1H), 7.26 (d, 1H, J=2.3 Hz), 7.38 (d, 2H, J=7.9 Hz), 8.02 (d, 2H, J=7.9 Hz).

(Z)-4-[2-(2,2,4,4-Tetramethylchroman-6-yl)-2-(trimethylsilyl)vinyl]benzoic acid (Compound 11)

Following General Procedure C, ethyl(Z)-4-[2-(2,2,4,4-tetramethylchroman-6-yl)-2-(trimethylsilyl)vinyl]benzoate (Compound 10, 0.48 g, 1.1 mmol) was hydrolyzed to give the title compound.

PNMR (300 MHz, CDCl$_3$)• −0.04 (s, 9H), 1.37 (s, 6H), 1.39 (s, 6H), 1.86 (s, 2H), 6.76 (d, 1H, J=8.3 Hz), 6.94 (dd, 1H, J=2.2, 8.3 Hz), 7.09 (d, 1H, J=2.2 Hz), 7.29 (s, 1H), 7.44 (d, 2H, J=8.2 Hz), 8.11 (d, 2H, J=8.2 Hz).

(5-Bromothiophen-2-yl)methyl tert-butyldiphenylsilyl ether (Compound 12)

Tert-butyldiphenylsilyl chloride (7.8 mL, 30.1 mmol) was added to a solution of 5-bromo(thiophen-2-yl)methyl alcohol (4.9 g, 25.1 mmol) and 9.7 mL of dimethylformamide. The solution was treated with imidazole (4.29 g, 62.8 mmol) and stirred overnight at room temperature. The solution was diluted with ether and washed with 2% aqueous HCl. The layers were separated and the aqueous layer was extracted with ether. The combined organic extracts were washed with brine, and dried (MgSO$_4$), and filtered, and the solvents were removed in vacuo. The residue was purified by silica gel chromatography (hexane) to produce the title compound.

PNMR (300 MHz, CDCl$_3$)• 1.10 (s, 9H), 4.80 (s, 2H), 6.56 (d, 1H, J=2.4 Hz), 6.88 (d, 1H, J=2.4 Hz), 7.38–7.50 (m, 8H), 7.70 (m, 4H).

5-[(Trimethylsilyl)ethynyl]thiophen-2-ylmethyl tert-butyldiphenylsilyl ether (Compound 13)

A round bottom flask was flame-dried under high vacuum. The vacuum was broken by the addition of dry argon, and the flask was allowed to cool to room temperature. The flask was charged with 2.16 g (5.0 µmmol) of (5-bromothiophen-2-yl)methyl tert-butyldiphenylsilyl ether (Compound 12), 2.12 mL (15 mmol) of (trimethylsilyl)acetylene, and 17.5 mL of triethylamine. The solution was purged with argon for 15 min and bis(triphenylphosphine)palladium (II) chloride (88 mg, 0.125 mmol) and copper (I) iodide (24 mg, 0.125 mmol) were added and the solution stirred at ambient temperature for 3 days. The solution was poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by silica gel chromatography (hexane) to give the title compound.

PNMR (300 MHz, CDCl$_3$)• 0.25 (s, 9H), 1.08 (s, 9H), 4.83 (s, 2H), 6.63 (d, 1H, J=3.8 Hz), 7.06 (d, 1H, J=3.8 Hz), 7.41 (m, 8H), 7.68 (overlapping ds, 4H).

(Z)-5-[2-(3,5,5,8,8-Pentamethyl-5,6,7,8-tetrahydronaphthalen-2-yl)-2-(trimethylsilyl)vinyl]thiophene-2-ylmethyl alcohol (Compound 14)

Following General Procedure A, 5-[(trimethylsilyl)ethynyl]thiophen-2-ylmethyl tert-butyldiphenylsilyl ether (Compound 13, 0.75 g, 1.8 mmol) and 2-bromo-3,5,5,8,8-pentamethyl-5,6,7,8-tetrahydronaphthalene (0.45 g, 1.67 mmol) were coupled to give the title compound.

PNMR (300 MHz, CDCl$_3$)• 0.2 (s, 9H), 1.42 (s, 6H), 1.43 (s, 6H), 1.83 (s, 4H), 2.34 (s, 3H), 4.95 (s, 2H), 6.97 (s, 1H), 7.04 (s, 2H), 7.19 (s, 1H), 7.21 (s, 1H).

Ethyl(Z)-S-[2-(3,5,5,8,8-pentamethyl-5,6,7,8-tetrahydronaphthalen-2-yl)-2-(trimethylsilyl)vinyl]thiophene-2-carboxylate (Compound 15)

Following General Procedure B, (Z)-5-[2-(3,5,5,8,8-pentamethyl-5,6,7,8-tetrahydronaphthalen-2-yl)-2-(trimethylsilyl)vinyl]thiophene-2-ylmethyl alcohol (Compound 14, 0.088 g, 0.213 mmol) was oxidized to give the title compound.

PNMR (300 MHz, CDCl$_3$)• −0.029 (s, 9H), 1.26 (s, 6H), 1.27 (s, 6H), 1.39 (t, 3H, J=7.1 Hz), 1.67 (s, 4H), 2.17 (s, 3H), 4.35 (q, 2H, J=7.1 Hz), 6.80 (s, 1H), 7.00 (d, 1H, J=3.8 Hz), 7.02 (s, 1H), 7.06 (s, 1H), 7.69 (d, 1H, J=3.8 Hz).

(Z)-5-[2-(3,5,5,8,8-Pentamethyl-5,6,7,8-tetrahydronaphthalen-2-yl)-2-(trimethylsilyl)vinyl]thiophene-2-carboxylic acid (Compound 16)

Following General Procedure C, ethyl(Z)-5-[2-(3,5,5,8,8-pentamethyl-5,6,7,8-tetrahydronaphthalen-2-yl)-2-(trimethylsilyl)vinyl]thiophene-2-carboxylate (Compound 15, 0.050 g, 0.11 mmol) was hydrolyzed to give the title compound.

PNMR (300 MHz, CDCl$_3$)• 0.04 (s, 9H), 1.26 (s, 6H), 1.27 (s, 6H), 1.67 (s, 4H), 2.18 (s, 3H), 7.02 (s, 1H), 7.04 (s, 1H), 7.05 (d, 1H, J=4.1 Hz), 7.26 (s, 1H), 7.79 (d, 1H, J=4.1 Hz).

(Z)-5-[2-(5,5,8,8-Tetramethyl-5,6,7,8-tetrahydronaphthalen-2-yl)-2-(trimethylsilyl)vinyl]thiophene-2-ylmethyl alcohol (Compound 17)

Following General Procedure A, 5-[(trimethylsilyl)ethynyl]thiophen-2-ylmethyl tert-butyldiphenylsilyl ether (Compound 13, 0.75 g, 1.8 mmol) and 2-bromo-5,5,8,8-tetramethyl-5,6,7,8-tetrahydronaphthalene (0.46 g, 1.62 mmol) were coupled to give the title compound.

PNMR (300 MHz, CDCl$_3$)• 0.2 (s, 9H), 1.42 (s, 6H), 1.43 (s, 6H), 1.83 (s, 4H), 4.95 (s, 2H), 6.97 (s, 1H), 7.04 (s, 2H), 7.19 (s, 1H), 7.21 (s, 1H).

Ethyl(Z)-5-[2-(5,5,8,8-tetramethyl-5,6,7,8-tetrahydronaphthalen-2-yl)-2-(trimethylsilyl)vinyl]thiophene-2-carboxylate (Compound 18)

Following General Procedure B, (Z)-5-[2-(3,5,5,8,8-tetramethyl-5,6,7,8-tetrahydronaphthalen-2-yl)-2-(trimethylsilyl)vinyl]thiophene-2-ylmethyl alcohol (Compound 17, 0.30 g, 0.753 mmol) was oxidized to give the title compound.

PNMR (300 MHz, CDCl$_3$)• −0.029 (s, 9H), 1.26 (s, 6H), 1.27 (s, 6H), 1.39 (t, 3H, J=7.1 Hz), 1.67 (s, 4H), 4.35 (q, 2H,

J=7.1 Hz), 6.80 (s, 1H), 7.00 (d, 1H, J=3.8 Hz), 7.02 (s, 1H), 7.06 (s, 1H), 7.69 (d, 1H, J=3.8 Hz).

(Z)-5-[2-(5,5,8,8-Tetramethyl-5,6,7,8-tetrahydronaphthalen-2-yl)-2-(trimethylsilyl)vinyl]thiophene-2-carboxylic Acid (Compound 19)

Following General Procedure C, ethyl(Z)-5-[2-(5,5,8,8-tetramethyl-5,6,7,8-tetrahydronaphthalen-2-yl)-2-(trimethylsilyl)vinyl]thiophene-2-carboxylate (Compound 18, 0.125 g, 0.284 mmol) was hydrolyzed to give the title compound.

PNMR (300 MHz, CDCl$_3$)• 0.04 (s, 9H), 1.26 (s, 6H), 1.27 (s, 6H), 1.67 (s, 4H), 7.02 (s, 1H), 7.04 (s, 1H), 7.05 (d, 1H, J=4.1 Hz), 7.26 (s, 1H), 7.79 (d, 1H, J=4.1 Hz).

4-[Diethyl(5,5,8,8-tetramethyl-5,6,7,8-tetrahydronaphthalen-2-yl]silylbenzyl alcohol (Compound 20)

To a −78° C. solution of 2-bromo-5,5,8,8-tetramethyl-5,6,7,8-tetrahydronaphthalene (1.34 g, 5.0 mmol) in 6.9 mL of THF was added n-butyllithium (1.6 M, 3.13 ml, 5.0 mmol). After ten minutes, the solution was added via canula to a B78° C. solution of diethyldichlorosilane (0.61 mL, 5.0 mmol) and THF (4.4 mL) and stirring continued for 1 hour. In a second flask containing 4-bromobenzyl tert-butyldiphenylsilyl ether (Compound 1, 3.19 g, 7.5 μmmol) and THF (2 mL) at −78° C. was added n-butyllithium (1.6 M, 4.69 mL, 7.5 mmol). After ten minutes, the contents of the second flask were added via canula to the first flask. After 30 minutes at −78° C., the reaction was quenched by the addition of 5 mL of saturated aqueous NH$_4$Cl. The solution was poured into a separatory funnel containing water and hexane. The layers were separated and the aqueous layer was extracted 3 times with hexane. The combined organic layers were washed once with brine, and dried over magnesium sulfate, and the solvents were removed under reduced pressure. The residue was dissolved in 20 mL of THF and treated with 3.2 g of tetrabutylammonium flouride (Tbaf) adsorbed onto silica gel (1–1.6 mmol flouride per gram). The suspension was stirred for 5 hours at room temperature and then the silica gel was washed with ether, and the separated ether extracts were dried over magnesium sulfate. The filtered solvents were removed under reduced pressure and the residue purified by silica gel chromatography (9:1, hexane:ethyl acetate) to give the title compound.

PNMR (300 MHz, CDCl$_3$)• 0.91–1.06 (m, 10H), 1.25 (s, 6H), 1.28 (s, 6H), 1.68 (s, 4H), 4.70 (s, 2H), 7.22–7.25 (overlapping ds, 2H), 7.35 (d, 2H, J=8.1 Hz), 7.44 (s, 1H), 7.53 (d, 1H, J=8.1 Hz).

Ethyl 4-[diethyl(5,5,8,8-tetramethyl-5,6,7,8-tetrahydronaphthalen-2-yl]silylbenzoate (Compound 21)

Following General Procedure B, 4-[diethyl(5,5,8,8-tetramethyl-5,6,7,8

Compound 21

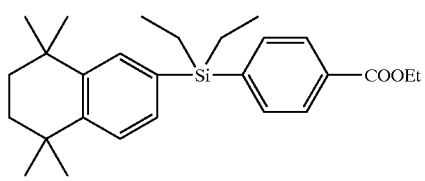

tetrahydronaphthalen-2-yl]silylbenzyl alcohol (Compound 20, 1.25 g, 3.30 mmol) was oxidized to give the title compound.

PNMR (300 MHz, CDCl$_3$)• 0.99–1.09 (m, 10H), 1.24 (s, 6H), 1.28 (s, 6H), 1.39 (t, 3H, J=7.1 Hz), 1.67 (s, 4H), 4.37 (q, 2H, J=7.1 Hz), 7.22–7.29 (overlapping ds, 2H), 7.42 (s, 1H), 7.60 (d, 2H, J=8.1 Hz), 8.00 (d, 1H, J=8.1 Hz).

4-[Diethyl(5,5,8,8-tetramethyl-5,6,7,8-tetrahydronaphthalen-2-yl]siybenzoic Acid (Compound 22)

Compound 22

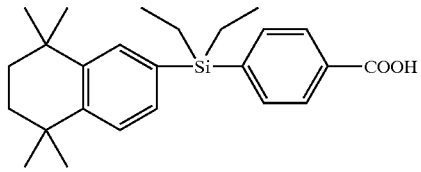

Following General Procedure C, ethyl 4-[diethyl(5,5,8,8-tetramethyl-5,6,7,8-tetrahydronaphthalen-2-yl]silylbenzoate (Compound 21, 0.650 g, 1.54 mmol) was hydrolyzed to give the title compound.

PNMR (300 MHz, CDCl$_3$)• 0.99–1.10 (m, 10H), 1.25 (s, 6H), 1.28 (s, 6H), 1.68 (s, 4H), 7.22–7.30 (overlapping ds, 2H), 7.42 (s, 1H), 7.64 (d, 2H, J=8.1 Hz), 8.07 (d, 1H, J=8.1 Hz).

4-[(Z)-(5,5-Dimethyl-8-p-tolyl-5,6-dihydronaphthalen-2-yl)trimethylsilanylvinyl]-benzyl Alcohol (Compound 23)

Compound 23

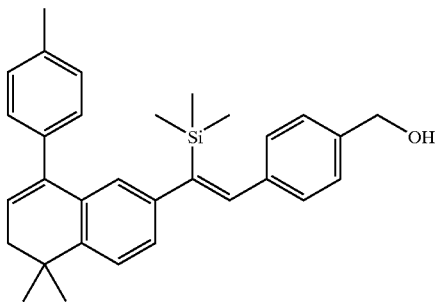

Following General Procedure A, 4-[(trimethylsilyl)ethynyl]benzyl tert-butyldiphenylsilyl ether and 6-bromo-1,1-dimethyl-4-p-tolyl-1,2-dihydronaphthalene (prepared as described in Klein, et al., U.S. Pat. No. 5,952,345) were coupled to give the title compound (Compound 23). PNMR (300 MHz, CDCl$_3$): δ0.13 (s, 9H), 1.47 (s, 6H), 2.48 (d, J=4.4 Hz, 2H), 2.54 (s, 3H), 4.82 (d, J=6.1 Hz, 2H), 6.10 (t, J=4.4 Hz, 1H), 7.00 (d, J=2.2 Hz, 1H), 7.18 (dd, J=2.2, 7.9 Hz, 1H), 7.30–7.45 (m, 10H).

Ethyl(Z)-4-[(5,5-Dimethyl-8-p-tolyl-5,6-dihydronaphthalen-2-yl)trimethylsilanylvinyl] benzoate. (Compound 24)

Compound 24

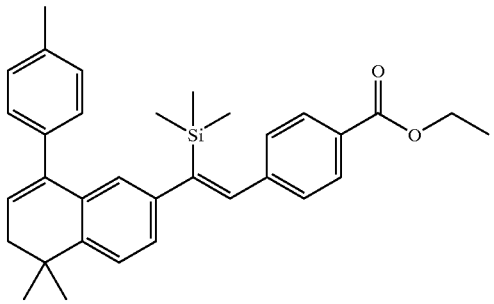

Following General Procedure B, 4-[(Z)-(5,5-dimethyl-8-p-tolyl-5,6-dihydronaphthalen-2-yl)trimethylsilanylvinyl] benzyl alcohol was oxidized to give the title compound (Compound 24). PNMR (300 MHz, CDCl$_3$): (Compound 34) 0.0 (s, 9H), 1.47 (s, 6H), 1.53 (t, J=7.0 Hz, 3H), 2.48 (d, J=4.7 Hz, 2H), 2.54 (s, 3H) 4.50 (q, J=7.0 Hz, 2H), 6.10 (t, J=4.7 Hz, 1H), 6.99 (d, J=2.0 Hz, 1H), 7.17 (dd, J=2.0, 7.9 Hz, 1H), 7.30–7.54 (m, 8H), 8.11 (d, J=8.2 Hz, 2H).

(Z)-4[(5,5-Dimethyl-8-p-tolyl-5,6-dihydronaphthalen-2-yl)trimethylsilanylvinyl]-benzoic Acid. (Compound 25)

Compound 25

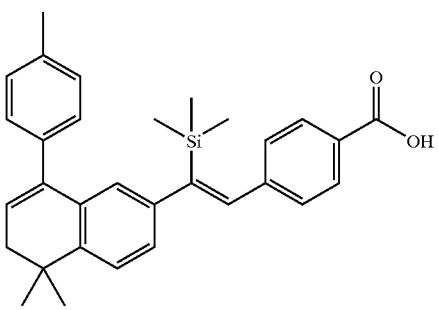

Following General Procedure C, ethyl(Z)-4-[(5,5-dimethyl-8-p-tolyl-5,6-dihydronaphthalen-2-yl) trimethylsilanylvinyl]benzoate was hydrolyzed to give the title compound (Compound 25). PNMR (300 MHz, CDCl$_3$): δ 0.0 (s, 9H), 1.47 (s, 6H), 2.48 (d, J=4.9 Hz, 2H), 2.54 (s, 3H), 6.10 (t, J=4.9 Hz, 1H), 6.98 (d, J 2.0 Hz, 1H), 7.16 (dd, J=2.0, 7.9 Hz, 1H), 7.30–7.60 (m, 8H), 8.15 (d, J=8.3 Hz, 2H).

(Z)-[4-(5,5-Dimethyl-8-phenyl-5,6-dihydronaphthalen-2-yl)trimethylsilanylvinyl]-benzyl Alcohol. (Compound 26).

Compound 26

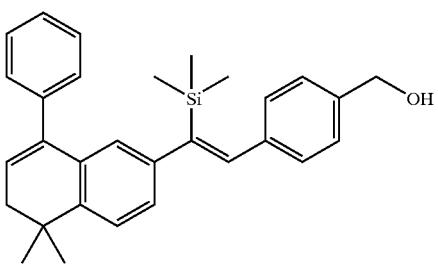

Following General Procedure A, 4-[(trimethylsilyl) ethynyl]benzyl tert-butyldiphenylsilyl ether and 6-bromo-1,1-dimethyl-4-phenyl-1,2-dihydronaphthalene (which can be prepared by the procedure described in Klein, et al., U.S. Pat. No. 5,952,345) were coupled to give the title compound (Compound 26). PNMR (300 MHz, CDCl$_3$): δ 0.0 (s, 9H), 1.49 (s, 6H), 2.50 (d, J=4.4 Hz, 2H), 4.80 (d, J=5.7 Hz, 2H), 6.13 (t, J=4.4 Hz, 1H), 6.98 (d, J=2.2 Hz, 1H), 7.21 (dd, J=2.2, 7.9 Hz, 1H), 7.31–7.60 (m, 7H).

Ethyl(Z)-4-[(5,5-Dimethyl-8-phenyl-5,6-dihydronaphthalen-2-Yl)trimethylsilanylvinyl] benzoate. (Compound 27)

Compound 27

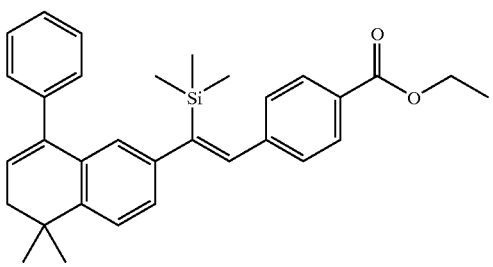

Following General Procedure B, (Z)-4-[(5,5-dimethyl-8-phenyl-5,6-dihydronaphthalen-2-yl)trimethylsilanylvinyl] benzyl alcohol was oxidized to give the title compound (Compound 27). PNMR (300 MHz, CDCl$_3$): δ 0.0 (s, 9H), 1.50 (s, 6H), 1.55 (t, J=Q7.4 Hz, 3H), 2.5.1 (d, J=4.8 Hz, 2H), 4.52 (q, J=7.4 Hz, 2H), 6.15 (t, J=4.8 Hz, 1H), 6.99 (d, J=2.2 Hz, 1H), 7.21 (dd, J=2.2, 7.9 Hz, 1H), 7.33 (s, 1H), 7.40–7.60 (m, 7H), 8.12 (d, J=8.3 Hz, 2H).

(Z)-4-[(5,5-Dimethyl-8-phenyl-5,6-dihydronaphthalen-2-yl)trimethylsilanylvinyl]-benzoic acid. (Compound 28)

Compound 28

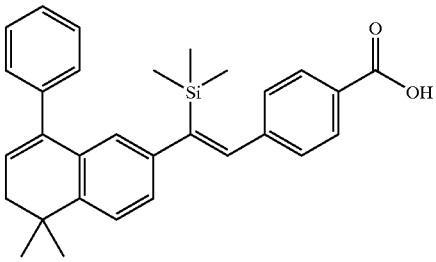

Following General Procedure C, ethyl(Z)-4-[(5,5-dimethyl-8-phenyl-5,6-dihydronaphthalen-2-yl) trimethylsilanylvinyl]benzoate was hydrolyzed to give the title compound (Compound 28). PNMR (300 MHz, CDCl$_3$): δ 0.13 (s, 9H), 1.49 (s, 6H), 2.50 (d, J=4.9 Hz, 2H), 6.13 (t, J=4.9 Hz, 1H), 6.97 (d, J=1.7 Hz, 1 H), 7.20 (dd, J=1.7, 7.9 Hz, 1H), 7.31 (s, 1H), 7.39–7.54 (m, 8H), 8.17 (d, J=8.4 Hz, 2H).

(Z)-4-{[8-(4-tert-Butylphenyl)-5,5-dimethyl-5,6-dihydronaphthalen-2-yl]-trimethylsilanylvinyl}benzyl Alcohol. (Compound 29)

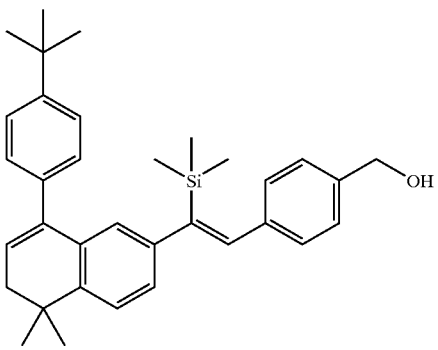

(Compound 29)

Following General Procedure A, 4-[(trimethylsilyl)ethynyl]benzyl tert-butyldiphenylsilyl ether and 6-bromo-4-(tert-butylphenyl)-1,1-dimethyl-1,2-dihydronaphthalene (which can be prepared by the procedure described in Klein, et al., U.S. Pat. No. 5,952,345) were coupled to give the title compound (Compound 29). PNMR (300 MHz, CDCl$_3$): δ 0.0 (s, 9H), 1.48 (s, 6H), 1.51 (s, 9H), 2.49 (d, J=4.8 Hz, 2H), 4.82 (d, J=4.8 Hz, 2H), 6.13 (t, J=4.8 Hz, 1H), 7.00 (d, J=1.7 Hz, 1H), 7.22 (dd, J=1.7, 7.9 Hz, 1H), 7.30–7.50 (m, 8H), 7.55 (d, J=8.8 Hz, 2H).

Ethyl(Z)-4-{[8-(4-tert-Butylphenyl)-5,5-dimethyl-5,6-dihydronaphthalen-2-yl]-trimethylsilanylvinyl}benzoate. (Compound 30)

(Compound 30)

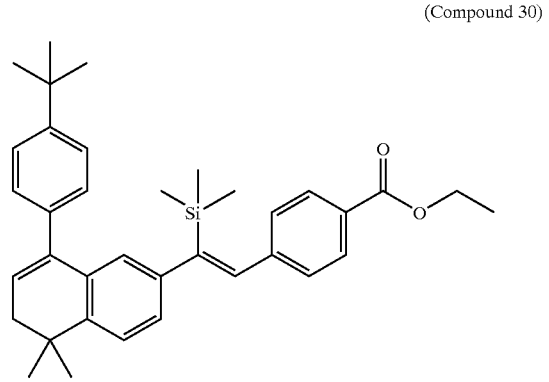

Following General Procedure B, (Z)-4-([8-(4-tert-butylphenyl)-5,5-dimethyl-5,6-dihydronaphthalen-2-yl] trimethylsilanylvinyl)benzyl alcohol was oxidized to give the title compound (Compound 30). PNMR (300 MHz, CDCl$_3$): δ 0.0 (s, 9H), 1.49 (s, 15H), 1.53 (t, J=7.1 Hz, 3H), 2.50 (d, J=4.4 Hz, 2H), 4.51 (q, J=7.1 Hz, 2H), 6.13 (t, J=4.4 Hz, 1H), 6.98 (d, J=2.2 Hz, 1H), 7.20 (dd, J=2.2, 8.0 Hz, 1H), 7.31 (s, 1H), 7.40–7.54 (m, 7H), 8.12 (d, J=8.4 Hz, 2H).

(Z)-4-{[8-(4-tert-Butylphenyl)-5,5-dimethyl-5,6-dihydronaphthalen-2-yl]-trimethylsilanylvinyl}benzoic Acid. (Compound 31)

(Compound 31)

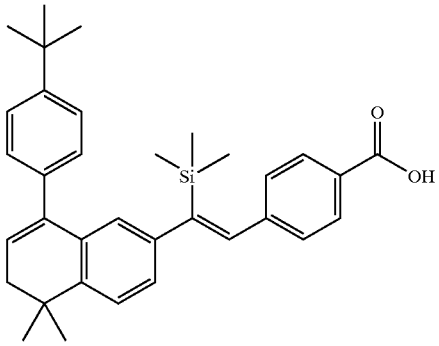

Following General Procedure C, ethyl(Z)-4-{[8-(4-tert-butylphenyl)-5,5-dimethyl-5,6-dihydronaphthalen-2-yl] trimethylsilanylvinyl}-benzoate was hydrolyzed to give the title compound (Compound 31). PNMR (300 MHz, CDCl$_3$): δ 0.0 (s, 9H), 1.49 (s, 15H), 2.50 (d, J=4.8 Hz, 2H), 6.13 (t, J=4.8 Hz, 1H), 6.96 (d, J=2.2 Hz, 1H), 7.20 (dd, J=2.2, 7.9 Hz, 1H), 7.31 (s, 1H), 7.44–7.54 (m, 7H), 8.18 (d, J=8.4 Hz, 2H).

(Z)-4-[2-(3,5-Di-tert-butylphenyl)-2-trimethylsilanylvinyl]benzyl alcohol. (Compound 32)

(Compound 32)

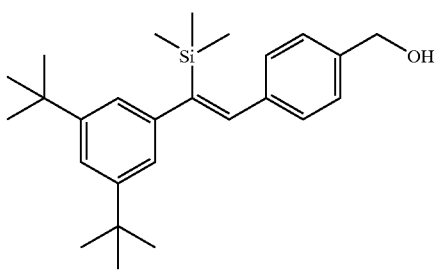

Following General Procedure A, 4-[(trimethylsilyl)ethynyl]benzyl tert-butyldiphenylsilyl ether and 1-bromo-3,5-Di-tert-butylbenzene (which can be prepared by the procedure described in Komen and Bickel *Synth. Commun*, 1996, 26, 1693–1698) were coupled to give the title compound (Compound 32). PNMR (300 MHz, CDCl$_3$) δ 7.40 (s, 4H), 7.33 (s, 2H), 7.08 (s, 1H), 7.07 (s, 1H), 4.78 (d, J=5.9 Hz, 1H), 1.41 (s, 18H), 0.00 (s, 9H).

41
Ethyl 4-[2-(3,5-Di-tert-butylphenyl)-2-trimethylsilanylvinyl]benzoate. (Compound 33)

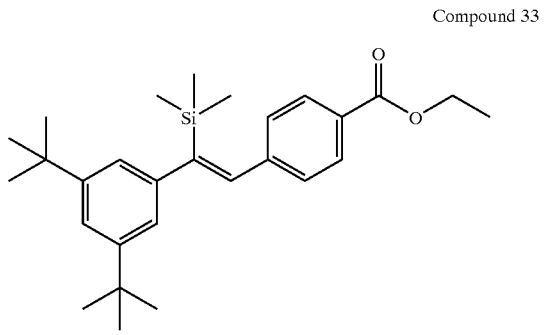

Compound 33

Following General Procedure B, (Z)-4-[2-(3,5-Di-tert-butylphenyl)-2-trimethylsilanylvinyl]benzyl alcohol was oxidized to give the title compound (Compound 33). PNMR (300 MHz, CDCl$_3$) δ 8.08 (d, J=8.4 Hz, 2H), 7.46 (d, J=8.5 Hz, 2H), 7.32 (m, 2H), 7.07 (s, 1H), 7.06 (s, 1H), 4.45 (q, J=7.2 Hz, 2H), 1.47 (t, J=7.2 Hz, 3H), 1.41 (s, 18H), 0.00 (s, 9H).

42
4-[2-(3,5-Di-tert-butylphenyl)-2-trimethylsilanylvinyl]benzoic Acid. (Compound 34)

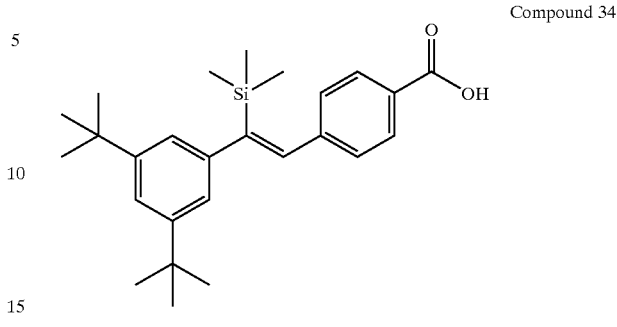

Compound 34

Following General Procedure C, ethyl 4-[2-(3,5-Di-tert-butylphenyl)-2-trimethylsilanylvinyl]-benzoate was hydrolyzed to give the title compound (Compound 34). PNMR (300 MHz, acetone-d6) δ 8.09 (d, J=8.2 Hz, 2H), 7.55 (d, J=7.9 Hz, 2H), 7.39 (m, 2H), 7.13 (s, 1H), 7.14 (s, 1H), 1.39 (s, 18H), 0.00 (s, 9H).

The examples set forth herein are meant to be illustrative only, and are not intended to limit the scope of the invention, which should be defined solely with reference to the claims that conclude this specification.

What is claimed is:

1. A method of treating an FXR-mediated pathological condition selected from hypercholesterolemia and hyperlipoproteinemia in a mammal comprising the step of administering to a mammal in need thereof a pharmaceutically acceptable composition comprising a compound of the formula:

formula (3)

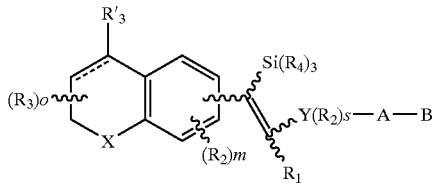

wherein the dashed line represents a bond or absence of a bond;

X is S, O, NR' where R' is H or alkyl of 1 to 6 carbons, or X is $(C(R_1)_2)_n$ where $R_1$ is H or alkyl of 1 to 6 carbons, and n is an integer having the value of 0 to 1;

$R_2$ is hydrogen, lower alkyl of 1 to 6 carbons, F, Cl, Br, 1, $CF_3$, fluoro substituted alkyl of 1 to 6 carbons, OH, SH, alkoxy of 1 to 12 carbons, or alkylthio of to 12 carbons, benzyloxy or $C_1$–$C_{12}$ alkylbenzyloxy;

$R_3$ is hydrogen, lower alkyl of 1 to 6 carbons or F;

m is an integer having the value of 0–3;

o is an integer having the value of 0–4 when the dashed line represents absence of a bond, and 0–3 when the dashed line represents a bond;

$R'_3$ is hydrogen, lower alky of 1 to 6 carbons, F or $(R_{15})_r$-phenyl, $(R_{15})_r$-naphthyl, or $(R_{15})_r$-heteroaryl where the heteroaryl group has 1 to 3 heteroatoms selected from the group consisting of O, S and H, r is an integer having the values of 0–5;

$R_4$ is alkyl of 1 to 8 carbons, or phenyl;

s is an integer having the value of 0–2;

Y is phenyl or naphthyl group, or heteroaryl selected from a group consisting of pyridyl, thienyl, furyl, pyridazinly, pyrimidinyl, pyrazinyl, thiazolyl, oxazolyl, imidazolyl and pyrrazolyl, said phenyl and heteroaryl groups being optionally substituted with one or two $R_2$ groups;

$R_{15}$ is independently H, F, Cl, Br, I, $NO_2$, $N(R_8)_2$, $NH(R_8)$, $COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

A is $(CH)_q$ where q is 0–5, lower branched chain alkyl having 3–6 carbons cycloalkyl having 3–6 carbons, alkenyl having 2–6 carbons and 1 or 2 double bonds, alkynyl having 2–6 carbons and 1 or 2 triple bonds;

B is hydrogen, COOH, $NO_2$, $P(O)(OH)_2$, $P(O)(OH)OR_8$, $P(O)(OR_8)_2$, $SO_2OH$, $SO_2(OR_8)$, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

2. A method in accordance with claim 1 where X is $(C(R_1)_2)_n$ and n is 1.

3. A method in accordance with claim 1 where X is S.

4. A method in accordance with claim 1 where X is 0.

5. A method in accordance with claim 1 where X is NR'.

6. A method in accordance with claim 1 where Y is phenyl.

7. A method in accordance with claim 1 where Y is thienyl.

8. A method in accordance with claim 1 wherein said compound has a structure of formula (3) where the dashed line represents a bond.

9. A method in accordance with claim 1 wherein said compound has a structure of formula (3) where the dashed line represents a bond.

10. A method of treating a hypercholesterolemic mammal comprising the steps: administering to a mammal in need thereof a pharmaceutically acceptable composition comprising an FXR antagonist having the following formula formula (3)

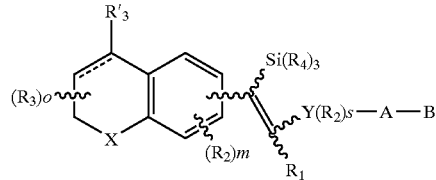

wherein the dashed line represents a bond or absence of a bond;

X is S, O, NR' where R' is H or alkyl of 1 to 6 carbons, or X is $(C(R_1)_2)_n$ where $R_1$ is H or alkyl of 1 to 6 carbons, and n is an integer having the value of 0 to 1;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 12 carbons, or alkylthio of 1 to 12 carbons, benzyloxy or $C_1$–$C_{12}$ alkylbenxyloxy;

$R_3$ is hydrogen, lower alkyl of 1 to 6 carbons or F;

m is an integer having the value of 0–3;

o is an integer having the value of 04 when the dashed line represents absence of a bond, and 0–3 when the dashed line represents a bond;

$R'_3$ is hydrogen, lower alky of 1 to 6 carbons, F or $(R_{15})_r$-phenyl, $(R_{15})_r$r-naphthyl, or $(R_{15})_r$-heteroaryl where the heteroaryl group has 1 to 3 heteroatoms selected from the group consisting of O, S and H, r is an integer having the values of 0–5;

$R_4$ is alkyl of 1 to 8 carbons, or phenyl;

Y is phenyl or naphthyl group, or heteroaryl selected from a group consisting of pyridyl, thienyl, furyl, pyridazinly, pyrimidinyl, pyrazinyl, thiazolyl, oxazolyl, imidazolyl and pyrrazolyl, said phenyl and heteroaryl groups being optionally substituted with one or two $R_2$ groups;

s is an integer having the value of 0–2;

$R_{15}$, is independently H, F, Cl, Br, I, $NO_2$, $N(R_8)_2$, $NH(R_8)$, $COR_8$, $NR_8CON(RB)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

A is $(CH_2)_q$ where q is 0–5, lower branched chain alkyl having 3–6 carbons cycloalkyl having 3–6 carbons, alkenyl having 2–6 carbons and 1 or 2 double bonds, alkynyl having 2–6 carbons and 1 or 2 triple bonds;

B is hydrogen, COOH, $NO_2$, $P(O)(OH)_2$, $P(O)(OH)OR_8$, $P(O)(OR_8)_2$, $SO_2OH$, $SO_2(OR_8)$, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$ $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of S-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

11. A method in accordance with claim 1 where $R_2$ is H and $R_4$ is ethyl.

12. A method in accordance with claim 11 where B is $CH_2OH$.

13. A method in accordance with claim 11 where B is $COOR_8$.

14. A method in accordance with claim 1 where the compound of formula (3) is

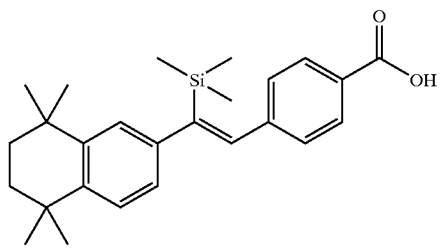

or a pharmaceutically acceptable salt thereof.

15. The method in accordance with claim 1 where the compound of formula (3) is

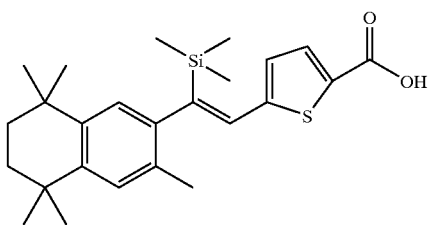

or a pharmaceutically acceptable salt thereof.

16. The method in accordance with claim 1 where the compound of formula (3) is

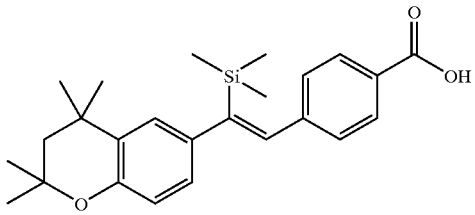

or a pharmaceutically acceptable salt thereof.

17. A method in accordance with claim 10 where $R_2$ is H and $R_4$ is ethyl.

18. A method in accordance with claim 17 where B is $CH_2OH$.

19. A method in accordance with claim 17 where B is $COOR_8$.

20. A method in accordance with claim 10 where X is $(C(R_1)_2)_n$ and n is 1.

21. A method in accordance with claim 10 where X is S.

22. A method in accordance with claim 10 where X is O.

23. A method in accordance with claim 10 where X is NR'.

24. A method in accordance with claim 10 where Y is phenyl.

25. A method in accordance with claim 10 where Y is thienyl.

26. A method in accordance with claim 10 where the compound of formula (3) is

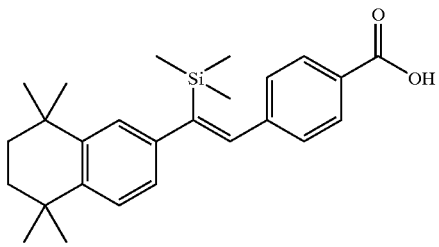

or a pharmaceutically acceptable salt thereof.

27. The method in accordance with claim 10 where the compound of formula (3) is

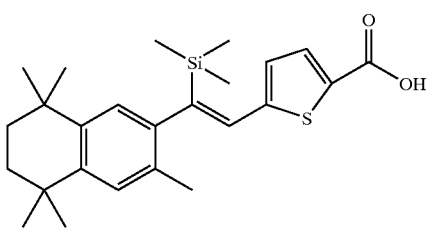

or a pharmaceutically acceptable salt thereof.

28. The method in accordance with claim 10 where the compound of formula (3) is

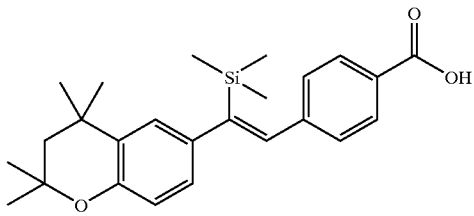

or a pharmaceutically acceptable salt thereof.

29. A method of treating an FXR-mediated pathological condition selected from hypercholesterolemia and hyperlipoproteinemia in a mammal comprising the step of administering to a mammal in need thereof a pharmaceutically acceptable composition comprising (Z)-5-[2-(5,5,8,8-tetramethyl-5,6,7,8-tetrahydronapthalen-2-yl)-2-(trimethylsilyl)vinyl]thiophene-2-carboxylic acid.

30. A method of treating a hypercholesterolemic mammal comprising the steps: administering to a mammal in need thereof a pharmaceutically acceptable composition comprising an FXR antagonist (Z)-5-[2-(5,5,8,8-tetramethyl-5,6,7,8-tetrahydronapthalen-2-yl)-2-(trimethylsilyl)vinyl]thiophene-2-carboxylic acid.

* * * * *

UNITED STATES PATENT AND TRADEMARK OFFICE
CERTIFICATE OF CORRECTION

PATENT NO. : 6,906,057 B1
DATED : June 14, 2005
INVENTOR(S) : Barry M. Forman, Richard L. Beard and Roshantha A. Chandraratna It is certified that error appears in the above-identified patent and that said Letters Patent is hereby corrected as shown below:

Column 55,
Line 25, first word, delete "1" and insert -- I -- therefor;
Line 56, after the words "A is" delete "$(CH)_q$" and insert -- $(CH_2)_q$ -- therefor;

Column 56,
Line 48, after "$C_1C_{12}$" delete "alkylbenxyloxy" and insert -- alkylbenzyloxy -- therefor;
Line 51, after the words "value of" delete "04" and insert -- 0-4 -- therefor;
Line 62, first word, delete "pyridazinly" and insert -- pyridazinyl -- therefor;

Column 57,
Line 2, after "$COR_8$" delete "$NR_8CON(RB)_2$" and insert -- $NR_8CON(R_8)_2$ -- therefor;
Line 17, last word, delete "$CR_7(OR_{12})_{21}$" and insert -- $CR_7(OR_{12})_2$, -- therefor; and
Line 25, after the words "group of" delete "S-10" and insert -- 5-10 -- therefor.

Signed and Sealed this

Sixteenth Day of August, 2005

JON W. DUDAS
*Director of the United States Patent and Trademark Office*